(12) United States Patent
Hayashi et al.

(10) Patent No.: US 8,264,326 B2
(45) Date of Patent: Sep. 11, 2012

(54) BIOMETRICS SENSOR

(75) Inventors: Kenshi Hayashi, Fukuoka (JP); Bunpei Yoshihiro, Shibuya-ku (JP)

(73) Assignees: Kyushu University, Fukuoka-shi (JP); Use Co., Ltd., Kurume-shi (JP)

( * ) Notice: Subject to any disclaimer, the term of this patent is extended or adjusted under 35 U.S.C. 154(b) by 733 days.

(21) Appl. No.: 12/439,374

(22) PCT Filed: Aug. 29, 2007

(86) PCT No.: PCT/JP2007/067242
§ 371 (c)(1),
(2), (4) Date: Jun. 3, 2009

(87) PCT Pub. No.: WO2008/026763
PCT Pub. Date: Mar. 6, 2008

(65) Prior Publication Data
US 2010/0007460 A1    Jan. 14, 2010

(30) Foreign Application Priority Data
Aug. 31, 2006   (JP) ................................. 2006-235949

(51) Int. Cl.
G01N 7/04       (2006.01)
G01N 33/497     (2006.01)
G01N 30/02      (2006.01)

(52) U.S. Cl. ...................... 340/5.82; 340/5.52; 340/5.81; 73/23.2; 73/23.22; 73/23.34; 73/23.35

(58) Field of Classification Search .................. 340/5.52, 340/5.81, 5.82; 73/23.2, 23.22, 23.34, 23.35
See application file for complete search history.

(56) References Cited

U.S. PATENT DOCUMENTS
4,347,732 A * 9/1982 Leary ........................... 73/31.05
6,244,096 B1   6/2001 Lewis
(Continued)

FOREIGN PATENT DOCUMENTS
JP    2000 148985    5/2000
(Continued)

OTHER PUBLICATIONS

Patricia Wallace, "Brief Communication", "Individual Discrimination of Humans by Odor", Physiology & Behavior, vol. 19, 1977, pp. 577-579.
(Continued)

Primary Examiner — Jennifer Mehmood
Assistant Examiner — Andrew Bee
(74) Attorney, Agent, or Firm — Oblon, Spivak, McClelland, Maier & Neustadt, L.L.P.

(57) ABSTRACT

A biometrics sensor includes a portion for sucking air, a molecular sieve portion for selectively passing or adsorbing specific gas contained in the air, a gas detecting section for detecting the concentration of gas passed through the molecular sieve or the remaining gas, and a data processing section for comparing the detection result with a prestored detection result, wherein the gas detecting section selectively detects predetermined gas, and the data processing section performs determination or probabilistic determination on an authentication object person by comparing the composition ratio of gas for each authentication object person with a prestored composition ratio.

5 Claims, 27 Drawing Sheets

U.S. PATENT DOCUMENTS

| | | | |
|---|---|---|---|
| 7,314,165 B2* | 1/2008 | Bonalle et al. | 235/380 |
| 2002/0000115 A1* | 1/2002 | Nakano et al. | 73/23.34 |
| 2003/0172717 A1* | 9/2003 | Kita et al. | 73/23.34 |
| 2005/0116810 A1* | 6/2005 | Beenau et al. | 340/5.52 |
| 2009/0081795 A1* | 3/2009 | Furton et al. | 436/63 |

FOREIGN PATENT DOCUMENTS

| | | |
|---|---|---|
| JP | 2000-148985 | 5/2000 |
| JP | 2002 22692 | 1/2002 |
| JP | 2003 192247 | 7/2003 |
| JP | 2003 281653 | 10/2003 |
| JP | 2005-129032 | 5/2005 |
| WO | WO 90/05965 | 5/1990 |
| WO | WO 99/08192 | 2/1999 |
| WO | WO 2006/006533 A1 | 1/2006 |

OTHER PUBLICATIONS

Amy C. Eklund, et al., "Polymorphisms in the HLA-linked Olfactory Receptor Genes in the Hutterites", Human Immunology 61, 2000, pp. 711-717.

Koide, et al., "Detection of a Hydrophobic Group Pattern of Smell Materials for Biometrics", 58th Joint Conference of Electrical and Electronics Engineers in Kyushu, 05-2P-19, p. 230, with English translation.

Japanese Office Action issued Apr. 24, 2012, in Japan Patent Application No. 2008-532148.

Supplementary European Search Report issued Apr. 26, 2012 in European Application No. 07806697.4.

* cited by examiner

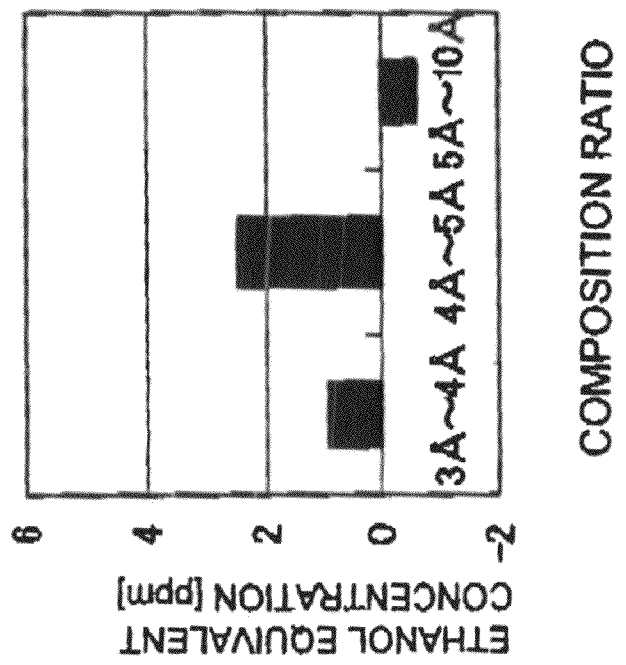

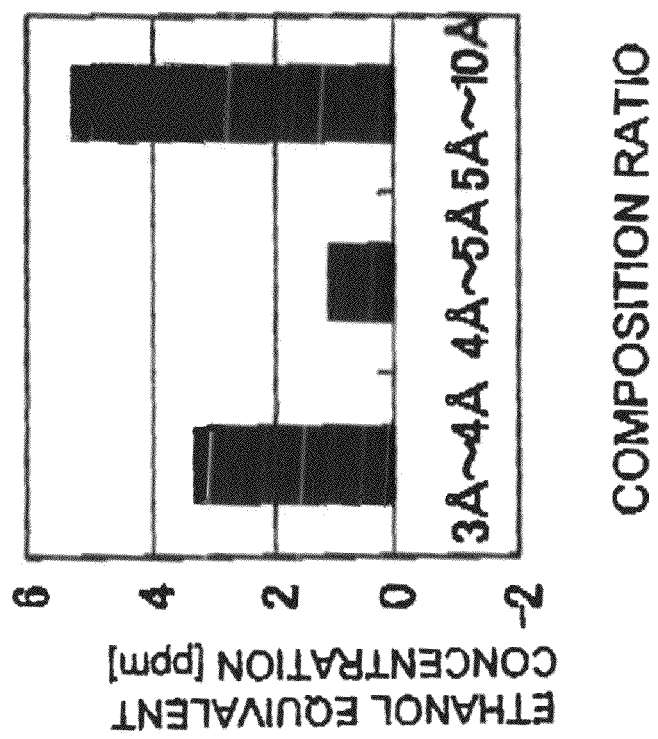
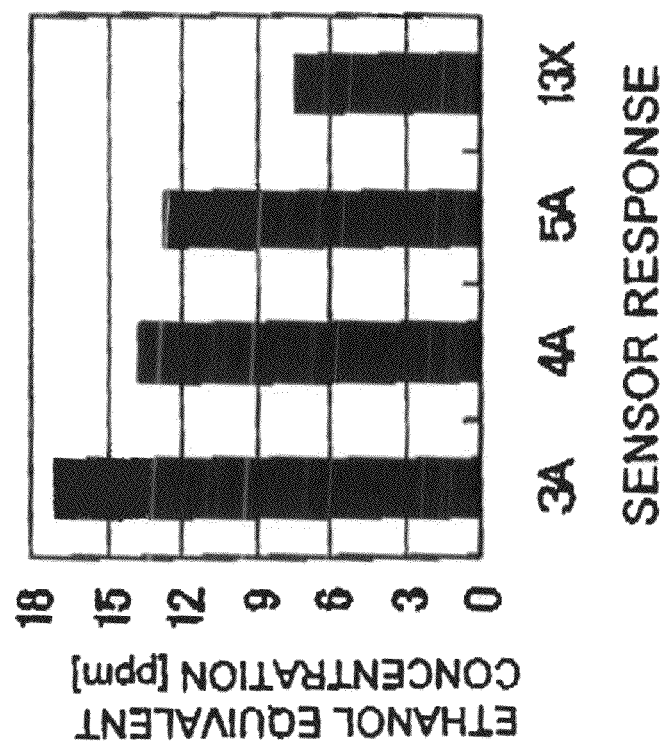

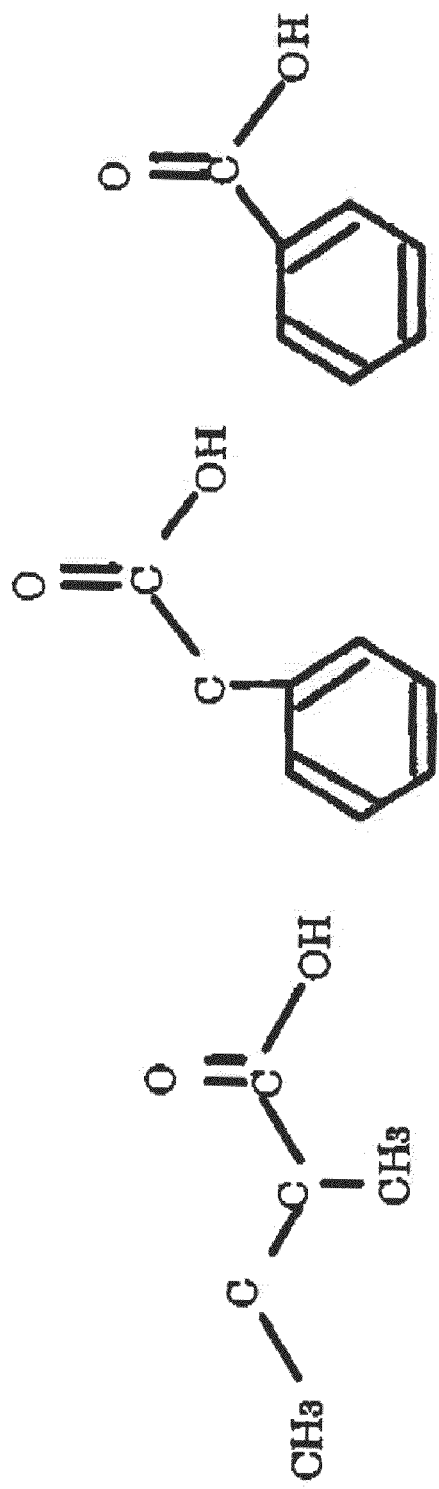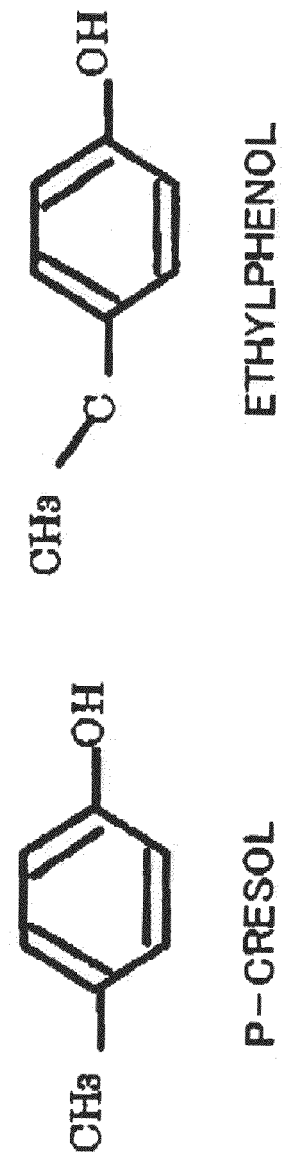
FIG.13

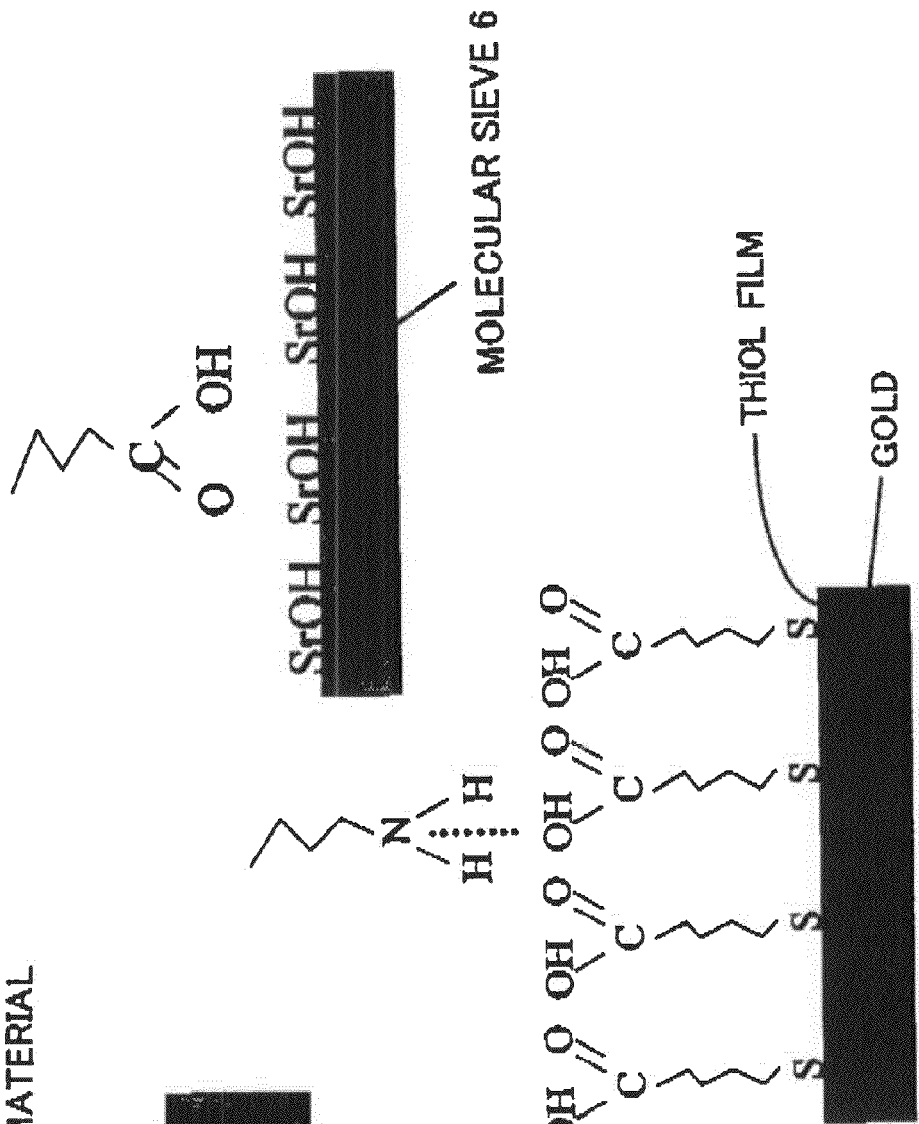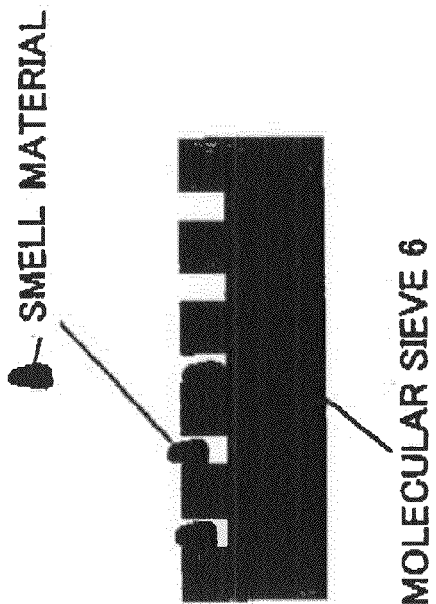

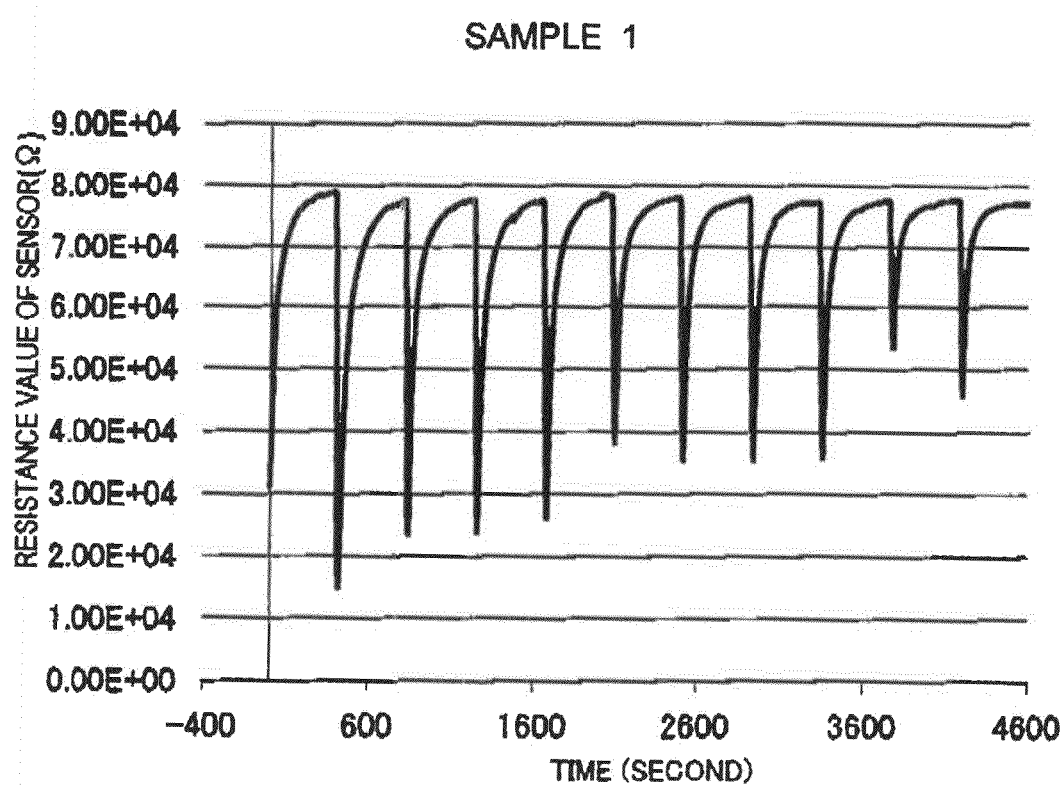

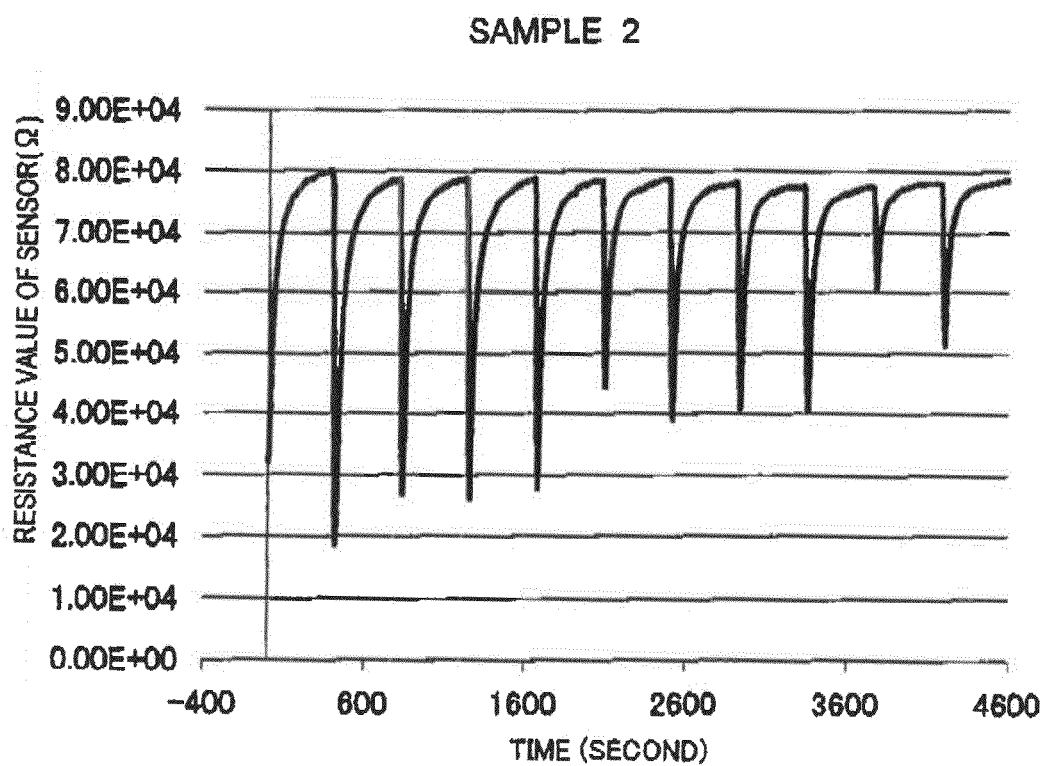

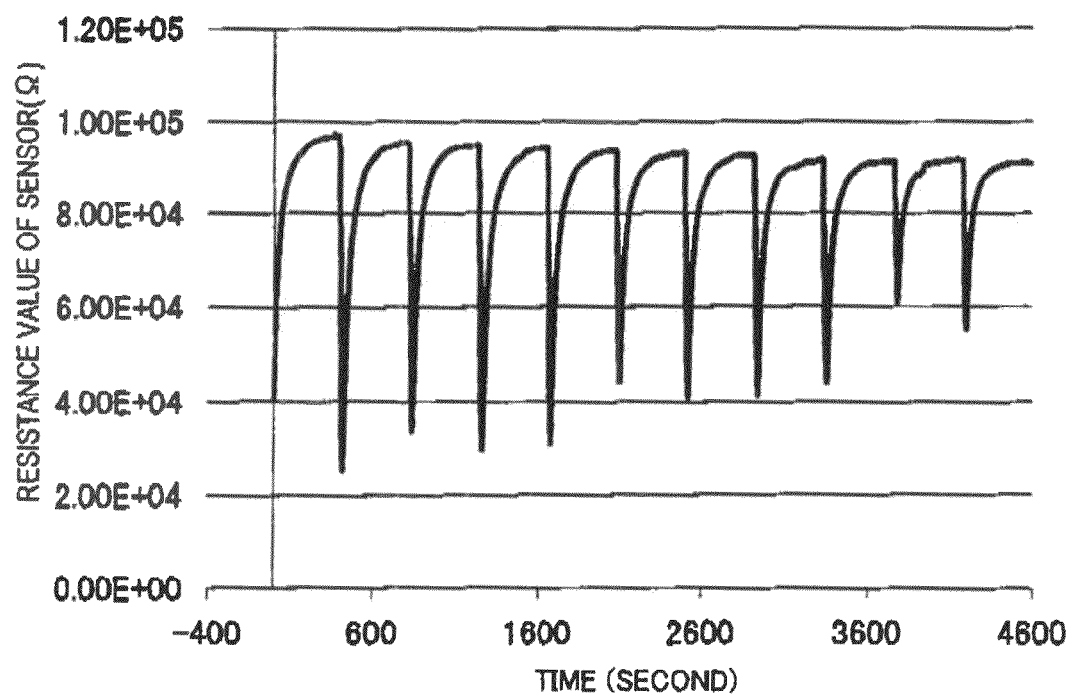

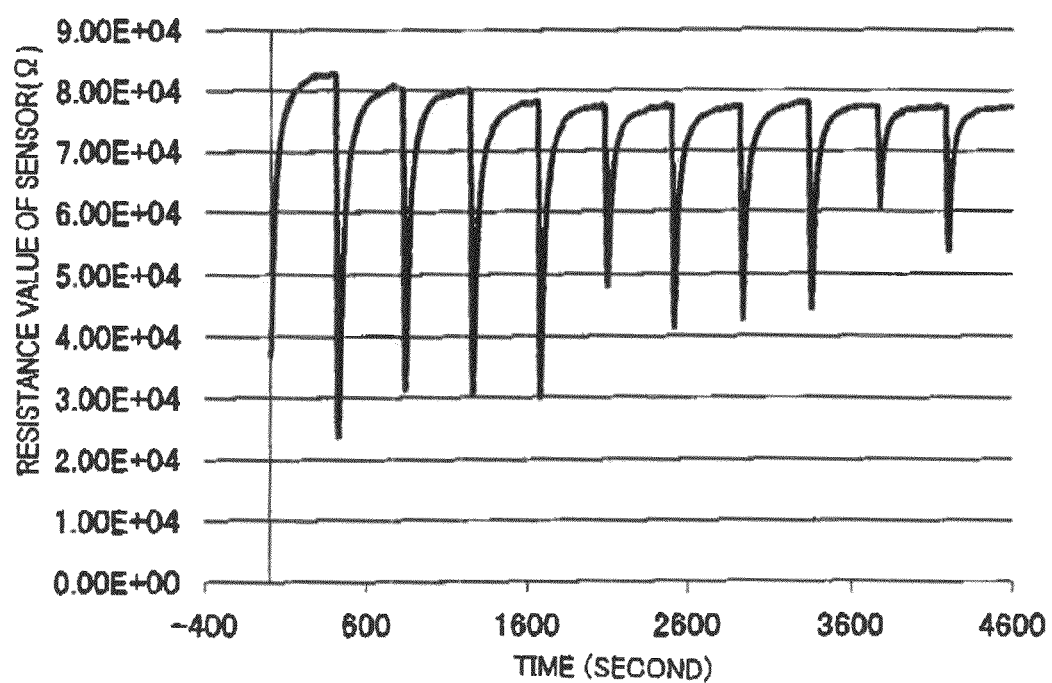

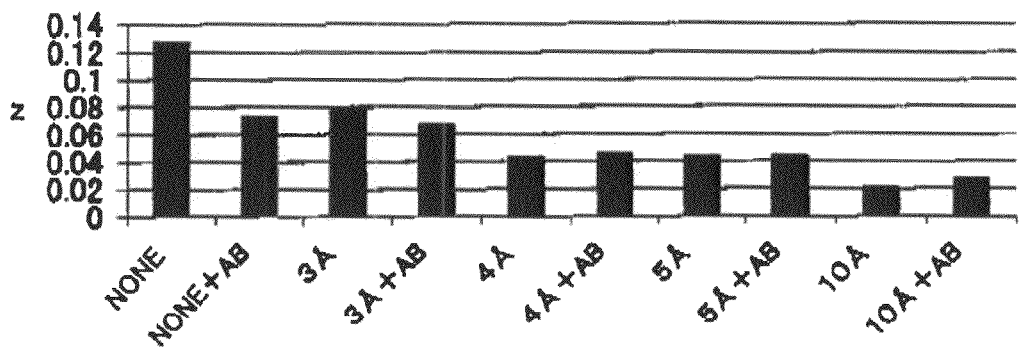
FIG.17(a) SAMPLE 1
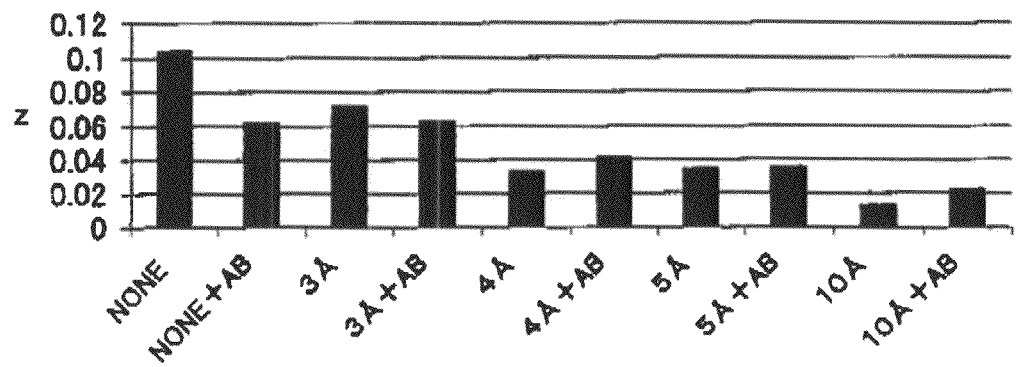
FIG.17(b) SAMPLE 2
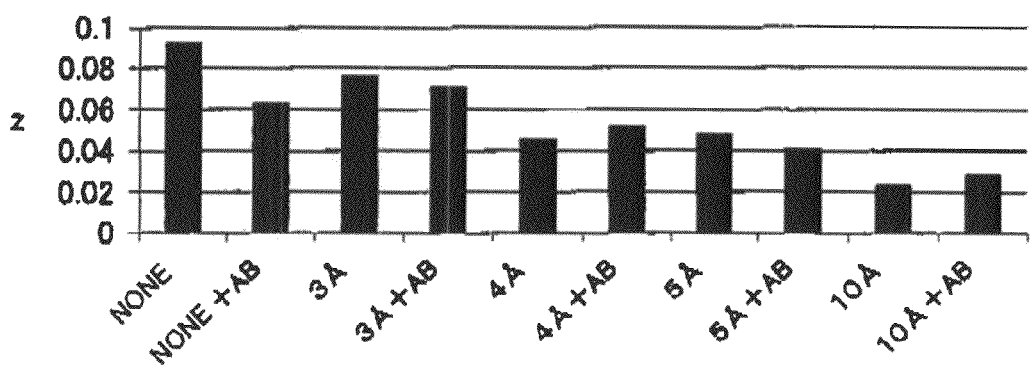
FIG.17(c) SAMPLE 3

BIOMETRICS SENSOR

TECHNICAL FIELD

The present invention relates to a biometrics sensor, which is used in an apparatus that detects survivors by analyzing smells around the scene of a disaster, an apparatus that performs medical diagnosis by analyzing a body smell of a measurement object person, and an apparatus that ensures security of an electronic hardware by determining a characteristic of a smell, such as a body smell of an authentication object person.

BACKGROUND ART

Conventionally, in order to find survivors, rescue dogs have been used in the scene of a disaster, thereby getting excellent results. However, since the rescue dogs need training and have a limited life, it has been required to mechanize a process of finding survivors in the scene of a disaster.

Further, people know through common experience that a body smell of an individual person generally varies in accordance with a condition of the body. In order to use smell data as a mechanism for carrying out medical diagnosis, digitization of the body smell has been required.

In recent years, with the development of an information-oriented society, in order to improve security in managing a variety of information, a personal authentication system that has high reliability and excellent convenience has been required.

The technical field is associated with the present invention. However, as an example, the case where a biometrics sensor is applied to an authentication system will be hereinafter described.

At the present time, as personal authentication methods, authentication methods based on a password or an ID card is generally used. However, these authentication methods are insufficient in terms of security in managing information, because there is a risk that the information maybe lost, robbed, or forged. Accordingly, an authentication method using biometrics that has no such risk has attracted attention.

The biometrics is a technique that identifies an individual person by using "information unique to an individual person", such as a physical characteristic or a behavioral characteristic. At the present time, a biometrics sensor generally means an apparatus using a fingerprint, an iris, or a vein pattern, and it has widely been put to practical use.

In general, it has been known that an individual person has a unique "odor type" as a body smell. For example, P. Wallance has reported that a person can distinguish another person by using a body smell diffused from a palm and has suggested that the kind of causative substance of a body smell can be affected by heredity and diet (Physiology & Behavior, vol. 19, pp. 577-579, Pergamon Press and Brain Research Publ., 1977). This is because a composition ratio of organic acids and alcohols in a body smell is different depending on an MHC (major histocompatibility complex) type. FIG. 13 shows materials whose composition ratios are reported to be different due to differences in the MHC types and the structural formulae of the materials.

[Known Example 1]

As a known example that is relatively similar to the present invention, there is a hydrophobic group pattern recognition sensor that is developed by the present inventors ("Detection of a Hydrophobic Group Pattern of Smell Materials for Biometrics" by Koide, Masunaga, Hayashi, and Toko in the 58th Joint Conference of Electrical and Electronics Engineers in Kyushu, page 230, 05-2P-19). The hydrophobic group pattern recognition sensor uses an oil droplet as a hydrophobic group absorption and recognition portion that absorbs a smell material. And this sensor monitors a fluorescence intensity variation of a fluorescent probe in the oil droplet using a fluorescent analysis method. As the fluorescent probe, diphenylhexatriene is used.

While, in the known example 1, the oil droplet is used and a smell material absorbed into the oil droplet is detected, the present invention is different from the known example 1 in that a liquid is not used, as will be described later.

[Known Example 2]

Japanese Patent Application Laid-Open No. 2000-148985 discloses a personal authentication system, where it is described that biological information including a body smell may be used as information to be input. However, in this document, the configuration of an input device for inputting a smell or the like is not specifically described.

[Known Example 3]

Japanese Patent Application Laid-open No. 2005-129032 discloses a biometrics authentication system. However, in this document, the specific configuration that is needed to input a smell as authentication information is not described.

[Known Example 4]

Amy C. Eklund et al. have analyzed samples of a Hutterite group using denaturing high performance liquid chromatography (DHPLC). In addition, based on the analysis result, Amy C. Eklund et al. have reported that an "allele" is formed by diversification of a receptor gene of a hallucination associated with human leucocyte antigen (HLA) and diversity of an odor type associated with the HLA can be found (Human Immunology 61, 711-717 (2000)). This document is also different from the present invention in that a liquid sample is used, similarly to the known example 1.

Further, in the case of a conventional biometrics sensor, for example, when an individual person is authenticated, the person needs to move his finger, eye or palm close to the biometrics sensor. For this reason, there is a disadvantage that it is troublesome for an authentication object person being authenticated. Accordingly, it is an object of the present invention to provide a biometrics sensor in which a smell or a body smell is used and which is advantageously capable of remotely measuring biological information to save the trouble of an authentication object person.

DISCLOSURE OF THE INVENTION

In order to achieve the above-described object, according to a first aspect of the present invention, a biometrics sensor includes a sucking section that sucks air in the vicinity of a measurement object person; a molecular sieve portion that selectively passes or absorbs a specific gas component contained in the sucked air; a gas detecting section that detects a concentration of a constituent component of gas passed through the molecular sieve portion or the specific gas component selectively passed through the molecular sieve portion or selectively absorbed into the molecular sieve portion remaining in the gas passed through the molecular sieve portion; and a data processing section that compares the detection result of the gas detecting section and a prestored detection result.

According to a second aspect of the present invention, the biometrics sensor has the configuration according to the first aspect and is used in a personal authentication system used in an electronic hardware. The measurement object person is an authentication object person, the molecular sieve portion absorbs organic acids, alcohols or amines and discharges other gas components, and the gas detecting section selectively detects a predetermined gas component from the discharged gas components. The data processing section includes an operation section and a storage section, and compares a composition ratio of organic acids, alcohols or amines for each authentication object person with a composition ratio obtained from the prestored detection result to perform determination or probabilistic determination on the authentication object person.

According to a third aspect of the present invention, in the configuration according to the second aspect, the molecular sieve portion is a filter for gas that separates the organic acids, the alcohols or the amines on the basis of a difference in molecule sizes, or a filter for gas that separates the organic acids, the alcohols or the amines on the basis of the presence or absence of an acid functionality or an amine group, and a smell detector is used as the gas detecting section.

According to a fourth aspect of the present invention, in the configuration according to the second aspect or the third aspect, the filter for gas that separates the organic acids, the alcohols or the amines on the basis of the difference in the molecule sizes has a configuration where each of filters comprising of absorbing materials having amounts of absorption depending on the molecule sizes is respectively arranged in parallel for every different molecule size. The filter for gas that separates the organic acids, the alcohols or the amines on the basis of the presence or absence of the acid functionality or the amine group absorbs the organic acids, the alcohols or the amines to a material having a strongly basic material film formed on a surface thereof or a material having a strongly acidic material film formed on a surface thereof to filtrate the gas. The biometrics sensor further includes a switching section that individually connects the gas detecting section and the filters.

The biometrics sensor of the present invention allows an authentication object person not to closely approximate to or come into contact with the sensor and remotely measures biological information. Accordingly, the biometrics sensor of the present invention can be easily used in searching survivors or medical diagnosis.

Further, according to the biometrics sensor of the present invention, when the biometrics sensor is used in a personal authentication system of an electronic hardware, a result of determination or probabilistic determination on an authentication object person is transmitted to the electronic hardware, such that an authentication result is used. Accordingly, if the biometrics sensor of the present invention is used together with another authentication method, it is possible to improve security in managing information.

BRIEF DESCRIPTION OF THE DRAWINGS

FIG. 6 is a graph illustrating a result that is obtained when a single component of ethanol of 100 ppm is measured as a sample, using a smell separating/detecting apparatus shown in FIG. 3.

FIG. 7 is a graph illustrating a result that is obtained when a single component of pentanol of 100 ppm is measured as a sample, using a smell separating/detecting apparatus shown in FIG. 3.

FIG. 13 is a diagram illustrating names of materials where composition ratios are different by differences in MHC types and composition formulas of the materials.

FIG. 14(a) is a schematic diagram of a molecular sieve using crystalline zeolite.

FIG. 14(b) is a schematic diagram of a resultant that is obtained by coating a nonporous glass bead with strontium hydroxide as a strong base.

FIG. 14(c) is a schematic diagram of a thiol film that absorbs amines.

FIG. 16(*b*) is a graph illustrating a relation between a response curve (R) showing a temporal variation in a resistance value of a sensor and a reference value curve (R0) of the sensor, in regards to FIG. 16(*a*).

FIG. 16(*c*) is a graph illustrating a relative concentration of a material contained in sample gas, which is calculated based on FIG. 16(*b*).

FIG. 17(*b*) is a graph illustrating a relative concentration of a smell material contained in sample gas 2 of a body smell, which is calculated based on FIG. 15(*b*).

FIG. 17(*c*) is a graph illustrating a relative concentration of a smell material contained in sample gas 3 of a body smell, which is calculated based on FIG. 15(*c*).

FIG. 17(*d*) is a graph illustrating a relative concentration of a smell material contained in sample gas 4 of a body smell, which is calculated based on FIG. 15(*d*).

FIG. 17(*e*) is a graph illustrating a relative concentration of a smell material contained in sample gas 5 of a body smell, which is calculated based on FIG. 15(*e*).

FIG. 17(*f*) is a graph illustrating a relative concentration of a smell material contained in sample gas 6 of a body smell, which is calculated based on FIG. 15(*f*).

FIG. 17(*g*) is a graph illustrating a relative concentration of a smell material contained in sample gas 7 of a body smell, which is calculated based on FIG. 15(*g*).

FIG. 17(*h*) is a graph illustrating a relative concentration of a smell material contained in sample gas 8 of a body smell, which is calculated based on FIG. 15(*h*).

BEST MODE FOR CARRYING OUT THE INVENTION

Figure 1:
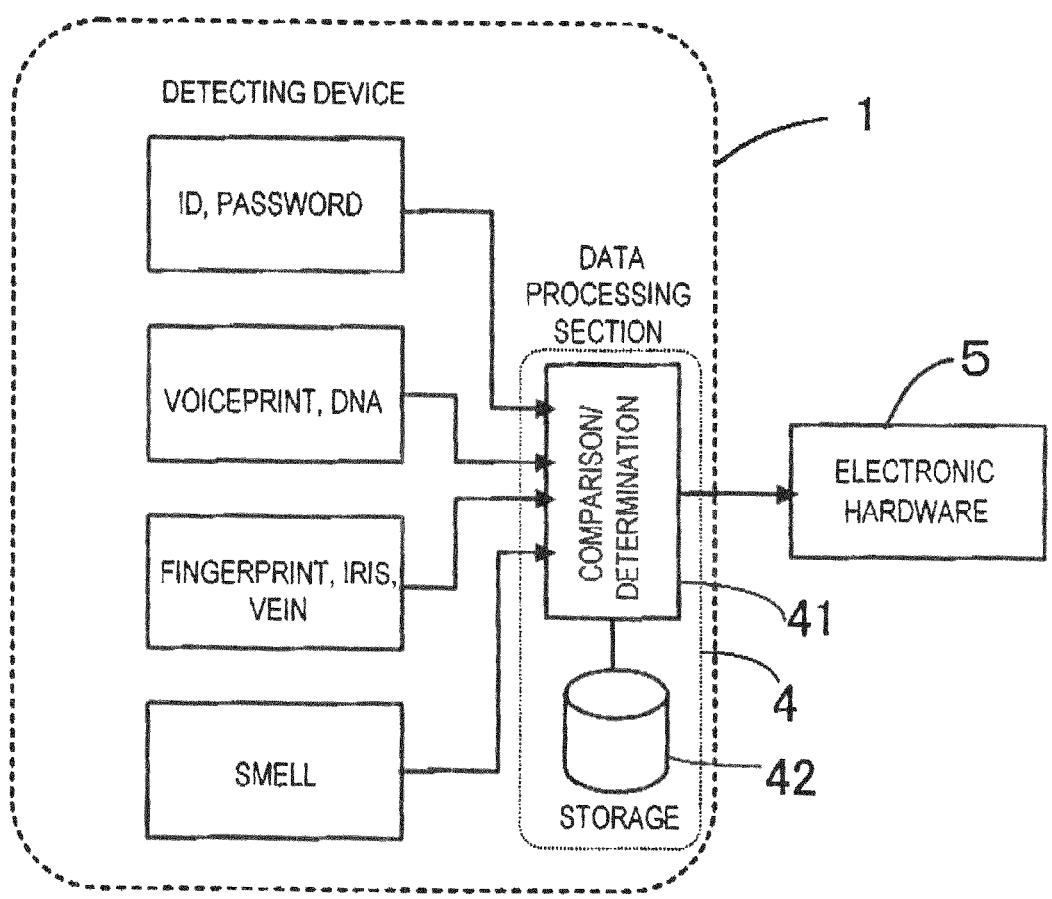
FIG. 1 is a block diagram illustrating an overview image of an authentication system 1 where a biometrics sensor of the present invention is applied.

Hereinafter, preferred embodiments of the present invention will be described in detail with reference to the accompanying drawings. In the description below, mechanisms that have the same function or similar functions are assigned with the same reference numerals unless there is a specific reason.

FIG. 1 is a block diagram illustrating an overview image of an authentication system 1 where the present invention is applied. For example, when an electronic hardware is a personal computer, an ID number and a password are input using a keyboard and compared with the previously registered ID number and password to determine whether they are equal to each other or not. When a person who inputs the ID number and the password is a registrant, the person is allowed to have access to the personal computer. In addition to the ID number and the password, patterns, such as a fingerprint, an iris, and a retina, may be used. Further, utilization of a voiceprint or DNA pattern is also suggested. Further, for example, when an electronic hardware is a controller that is related to starting of an automobile, a system that allows an engine to start after performing fingerprint authentication in addition to authentication through the presence or absence of a key is known.

Figure 2:
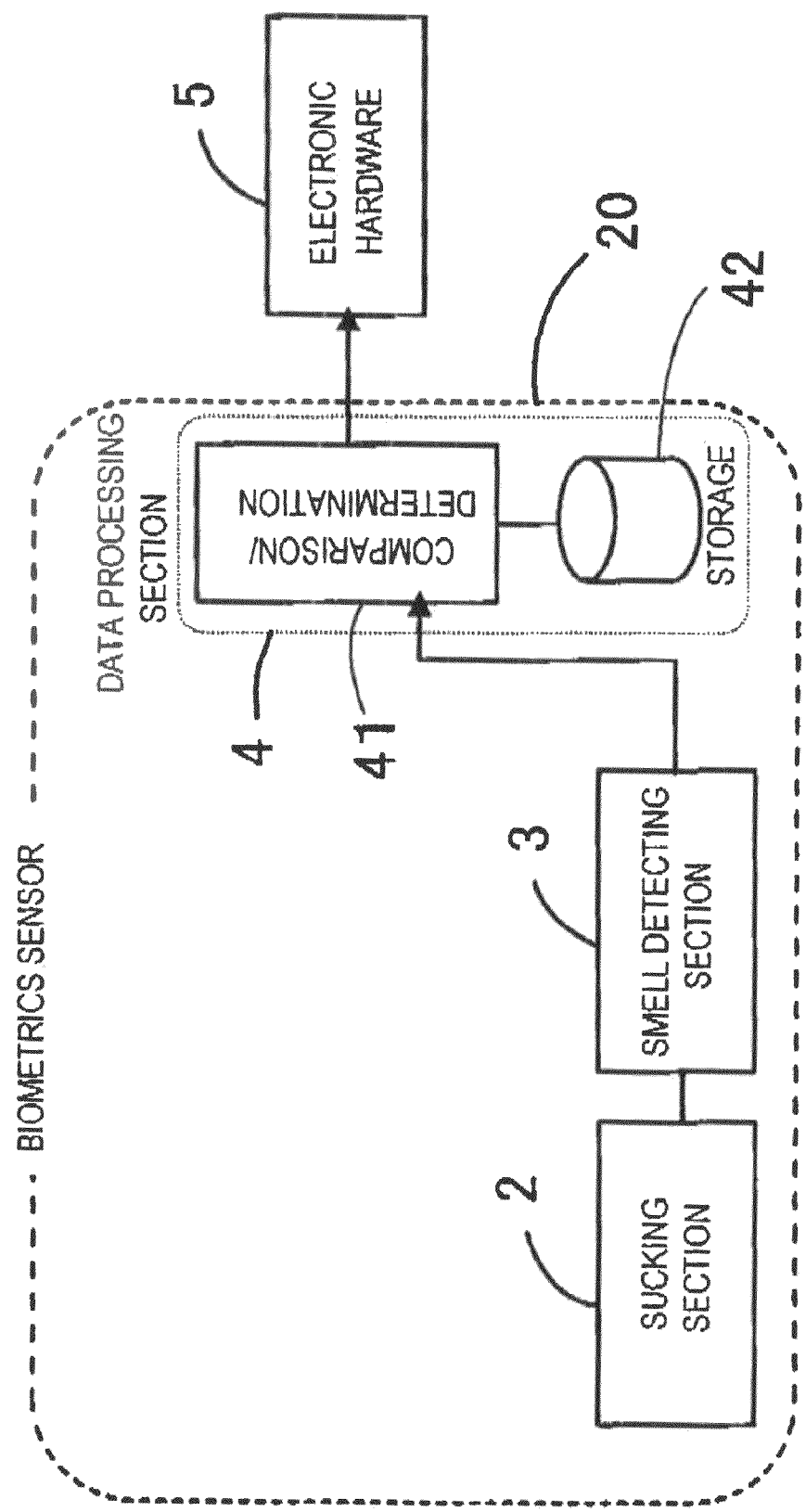
FIG. 2 is a block diagram illustrating a biometrics sensor of the present invention.

The present invention extracts a characteristic of a smell such as a body smell of an authentication object person and uses the extracted smell characteristic for authentication. If the present invention is used together with another authentication method, a security effect can obviously be improved. FIG. 2 is a block diagram illustrating a biometrics sensor 20 of the present invention. The biometrics sensor 20 includes a sucking section 2, a smell detecting section 3, and a data processing section 4.

First, in order to collect a smell, air in the vicinity of an authentication object person is sucked into the biometrics sensor 20 by the sucking section 2. Next, organic acids and alcohols that are contained in the sucked air are detected by the smell detecting section 3. The detection result can be used for classification of authentication object persons. Since the detection result varies as an absolute value but is constant as a relative value with respect to other gas components, a composition ratio of the organic acids and the alcohols is calculated. Further, the composition ratio is previously registered in the data processing section 4 together with other indices such as an ID number as an archive of a database. Using the database, a corresponding person is searched for based on another input of, for example, an identification (ID) number. If the difference between the registered data and the detection result is within a predetermined permitted range and valid, the data processing section 4 determines that the corresponding person of the data is an authentication object person. The data processing section 4 includes an operation section 41 that performs comparison and determination operations and a storage section (storage) 42 that stores data. The determination result from the operation section 41 is transmitted to the electronic hardware 5 as a signal that allows an operation so as to use the authentication result.

That is, if the corresponding person can be identified to be a registered member, the utilization of the electronic hardware 5 is allowed. In this case, the electronic hardware 5 has a function of receiving the authentication result from the authentication apparatus and allowing utilization or allowing access to certain data. The data processing section 4 may also be configured as a program in the electronic hardware 5 instead of being configured as an independent device.

In this way, the present invention measures the "odor type" and performs biometrics. That is, as described below, the present invention separates and detects organic acids and alcohols causing the "odor type" on the basis of a difference in molecule sizes and the presence or absence of an acid functionality and measures a composition ratio of the smell materials, thereby realizing biometrics based on the smell.

Figure 3:
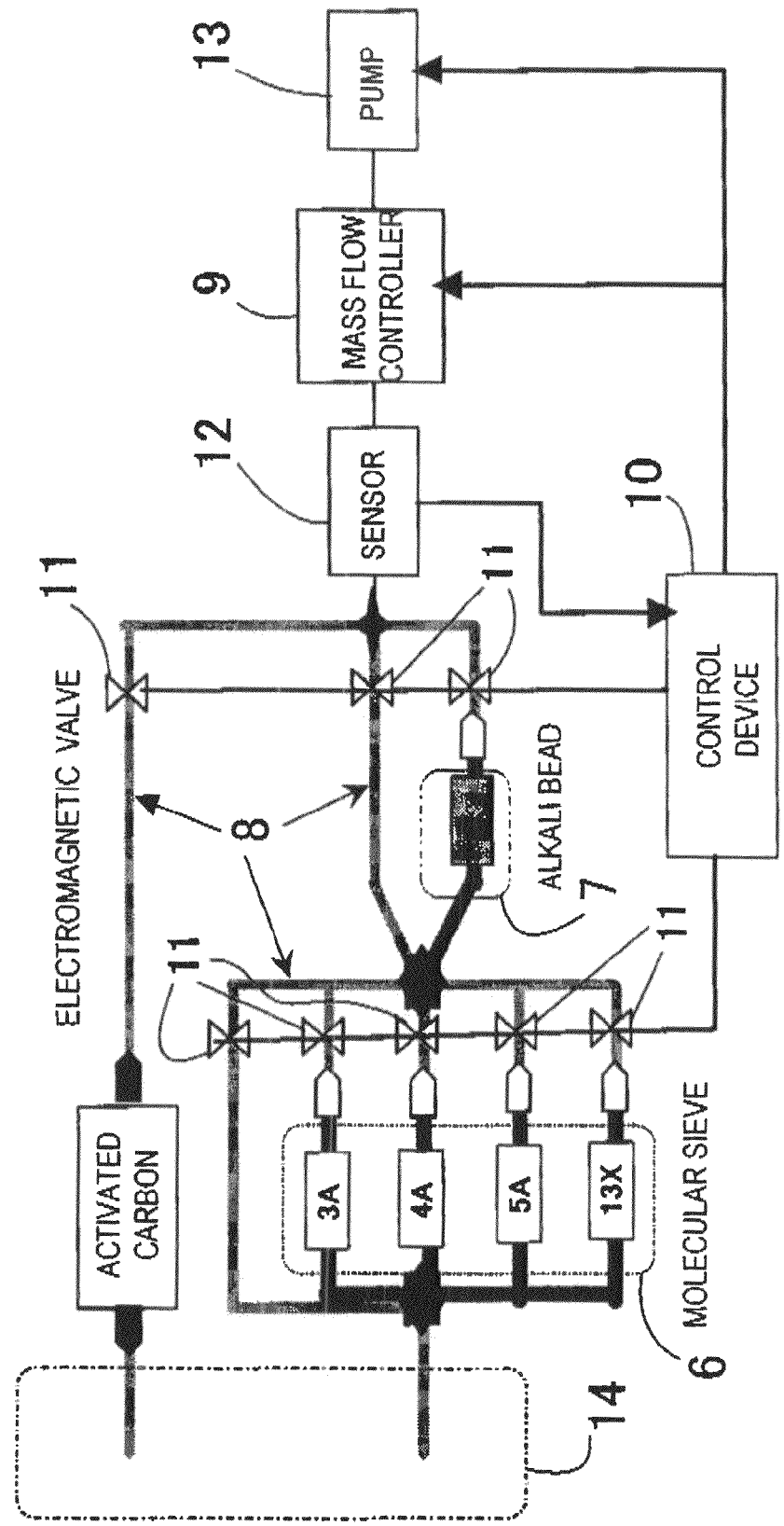
FIG. 3 is a block diagram illustrating a smell separating/detecting apparatus that separates and detects smell materials of organic acids or alcohols on the basis of a difference in molecule sizes and the presence or absence of an acid functionality.

FIG. 3 shows an example of a smell separating/detecting apparatus that separates and detects smell materials of organic acids or alcohols on the basis of a difference in molecule sizes and the presence or absence of an acid functionality. A sucking section, a molecular sieve portion, and a gas detecting section of the biometrics sensor of the present invention can be configured by the smell separating/detecting apparatus shown in FIG. 3. The molecular sieve portion of the smell separating/detecting apparatus shown in FIG. 3 corresponds to the molecular sieve portion of the biometrics sensor of the present invention, and is constituted by a molecular sieve 6 (registered trademark) (manufactured by KANTO CHEMICAL CO., INC.) and an alkali bead 7 (manufactured by SHINWA CHEMICAL INDUSTRIES LTD.). The air that is sucked by the sucking section 14 corresponding to the sucking section of the biometrics sensor of the present invention passes through the molecular sieve 6 or the alkali bead 7. The molecular sieve 6 is used for separation on the basis of the molecule sizes, and absorption by the alkali bead 7 is used for separation on the basis of the acid functionality.

In this case, the molecular sieve is crystalline zeolite that is aluminosilicate having regular pores. FIG. 14(*a*) shows a schematic diagram of the molecular sieve. The pore has a size of a molecule order. Thus, the molecular sieve has a nano structure with an adsorption site of a specific molecule size, and has a function of molecular sieving that selectively absorbs a material according to the pore diameter. The molecular sieve 6 that constitutes the molecular sieve portion of the smell separating/detecting apparatus shown in FIG. 3 includes four types of product segmentations of 3A, 4A, 5A, and 13X. "A" represents a unit (Angstrom) of an approximate size of a hole, and the monocular sieves of 3A, 4A, 5A, and 13X respectively have pores having diameters of about 3 Å, 4 Å, 5 Å, and 10 Å and have a nano structure that has an adsorption site of a specific molecule size. For example, in the molecular sieve of 3A, a material that has a diameter less than 3 Å is absorbed into the pore of the molecular sieve and trapped. However, since a material that has a diameter of 3 Å or more cannot be absorbed into the pore, the material is not trapped. In the molecular sieve of 4A, a material that has a diameter less than 4 Å can be absorbed, but a material that has a diameter of 4 Å or more cannot be absorbed. That is, a chemical material whose molecule size is in a range of 3 to 4 Å can be detected by comparing absorptions to the molecular sieves of 3A and 4A.

The alkali bead 7 that constitutes the molecular sieve portion together with the molecular sieve 6 is formed by coating a nonporous glass bead with strontium hydroxide as a strong base and can selectively absorb only the acids. FIG. 14(*b*) shows a schematic diagram of the alkali bead 7. Accordingly, organic acids are trapped, but alcohols that are not acid are not trapped. FIG. 14(*c*) shows a state where amines are absorbed into a terminal carboxyl group of a thiol film that coats a surface of a metal such as Au. As such, a monomolecular film having a terminal that interacts with a specific functional group is formed in the alkali bead 7.

Main passage 8 that constitutes the smell separating/detecting apparatus shown in FIG. 3 is formed by a tube of fluororesin, such as Teflon (registered trademark), and the molecular sieve 6 and the alkali bead 7 are each sealed in a column ($\phi$ 4.0 mm, length of 50 mm) in the passage. In order to keep a gas flow rate constant in each passage system, a mass flow controller 9 is inserted before a pump 13 to control the gas flow rate. An opening/closing control of an electromagnetic valve 11 that is provided in each passage is performed using a control device 10 (computer). By changing the passage by controlling the opening/closing of the electromagnetic valve 11, it is possible to filtrate the smell materials into any gas component of a molecule size of 10 Å or more, 5 Å or more, 4 Å or more, and 3 Å or more. In addition, it is possible to measure the contents of the smell materials having the molecule sizes of 3 to 4 Å, 4 Å to 5 Å, and 5 to 10 Å that are contained in the sample by comparing the responses from the smell sensor 12, which will be described below. Further, it is possible to measure whether molecules include an acid functionality by using the passage to the alkali bead 7.

The separated smell material is detected by the smell sensor 12. The smell sensor 12 corresponds to the gas detecting section of the biometrics sensor of the present invention, and in the smell separating/detecting apparatus shown in FIG. 3, an oxide semiconductor smell sensor (FIGARO TGS2600) is used. The oxide semiconductor smell sensor is an oxide semiconductor gas sensor using a characteristic of an electrical resistance being changed when combustible gas is absorbed into an oxide semiconductor heated to a high temperature. A resistance value of the sensor is measured by a digital multimeter.

In this case, for detecting the smell material is detected, it is possible to use an electrochemical impedance gas sensor where a smell material is diffused in an electrolyte, an electrochemical gas sensor that detects a change in a contact potential difference, a quartz crystal oscillator (QCM) sensor where a film having molecule selectivity is formed on an oscillator surface, a sensor using a characteristics of a resonance frequency of surface plasmon resonance (SPR) being changed in a surface state or the like, in addition to the oxide semiconductor gas sensor.

Figure 4:
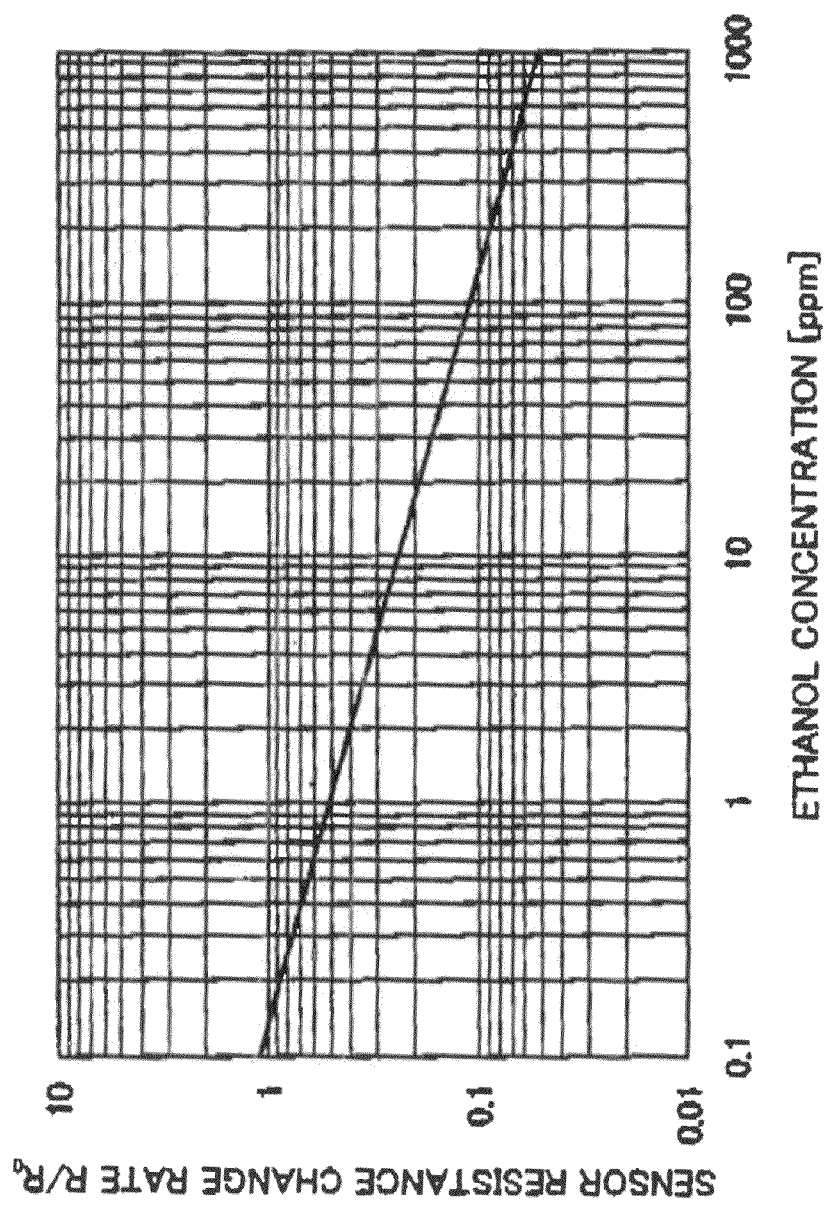
FIG. 4 is a graph illustrating an ethanol sensitivity characteristic of an oxide semiconductor sensor that is used in a smell separating/detecting apparatus shown in FIG. 3.

The oxide semiconductor gas sensor has sufficient sensitivity in measuring a body smell, but molecule selectivity of the sensor with respect to organic gas is low. An ethanol sensitivity characteristic of the oxide semiconductor sensor that is used as the smell sensor 12 is shown in FIG. 4. Since the sensitivity characteristic is different for each measured material, a change in the resistance value cannot be converted into a gas concentration when the measurement object is not known. In the characteristic evaluation that is described below, since measurement is made in the case where samples other than ethanol or a plurality of materials are mixed, a concentration (ethanol equivalent concentration) when measurement gas is assumed as ethanol is calculated as a reference of a sample gas concentration.

[Characteristic Evaluation Test]

(1) Evaluation of Separation Performance Based on a Molecule Size of a Single Smell Component A single component sample of each of ethanol, pentanol, and acetic acid of 100 ppm is prepared and used to evaluate separation performance by the molecule size with respect to the smell separating/detecting apparatus shown in FIG. 3. Table 1 shows chemical formulas and molecule sizes of measured materials.

TABLE 1

| Smell material | Chemical formula | Molecule size (Å) |
| --- | --- | --- |
| Ethanol | $C_2H_5OH$ | 4.08 |
| Pentanol | $C_5H_{11}OH$ | 6.24 |
| Acetic acid | $CH_3COOH$ | 3.16 |

(2) Evaluation of Separation Performance Based on Molecule Sizes of a Plurality of Smell Components Further, using a two component mixed sample prepared to contain 100 ppm each of ethanol and pentanol and a three component mixed sample prepared to contain 100 ppm each of ethanol, pentanol and acetic acid, separation performance by the molecule sizes is evaluated with respect to the smell separating/detecting apparatus shown in FIG. 3.

(3) Evaluation of Separation Performance Based on the Presence or Absence of an Acid Functionality Further, in a single sample of each of ethanol and acetic acid that are prepared to have the amount of 100 ppm, separation based on the presence or absence of an acid functionality is verified using an alkali bead.

(4) Evaluation of Body Smell Measurement Performance

Further, smells of humans are sampled and measured. A T-shirt worn by each test object person for one night is sealed in a sample bag and heated at a temperature of 60° C. for two hours, and concentrated gas is measured as a sample. The experiment is made by performing measurement with respect to a sample of each of test object persons A and B three times and calculating an average of the measured values.

In order to appropriately perform the characteristic evaluations of (1) to (4), first, parameters of the apparatus are determined as follows. The time when a smell material of 100 ppm is measured is set as a reference, the amount of the molecular sieve that is filled in a column is fixed to 0.30 g and a flow rate of air is fixed to 130 ml/min. Under the set conditions, each sample gas is absorbed for 100 seconds and a temporal change in sensor resistance is measured during this period.

Figure 5:
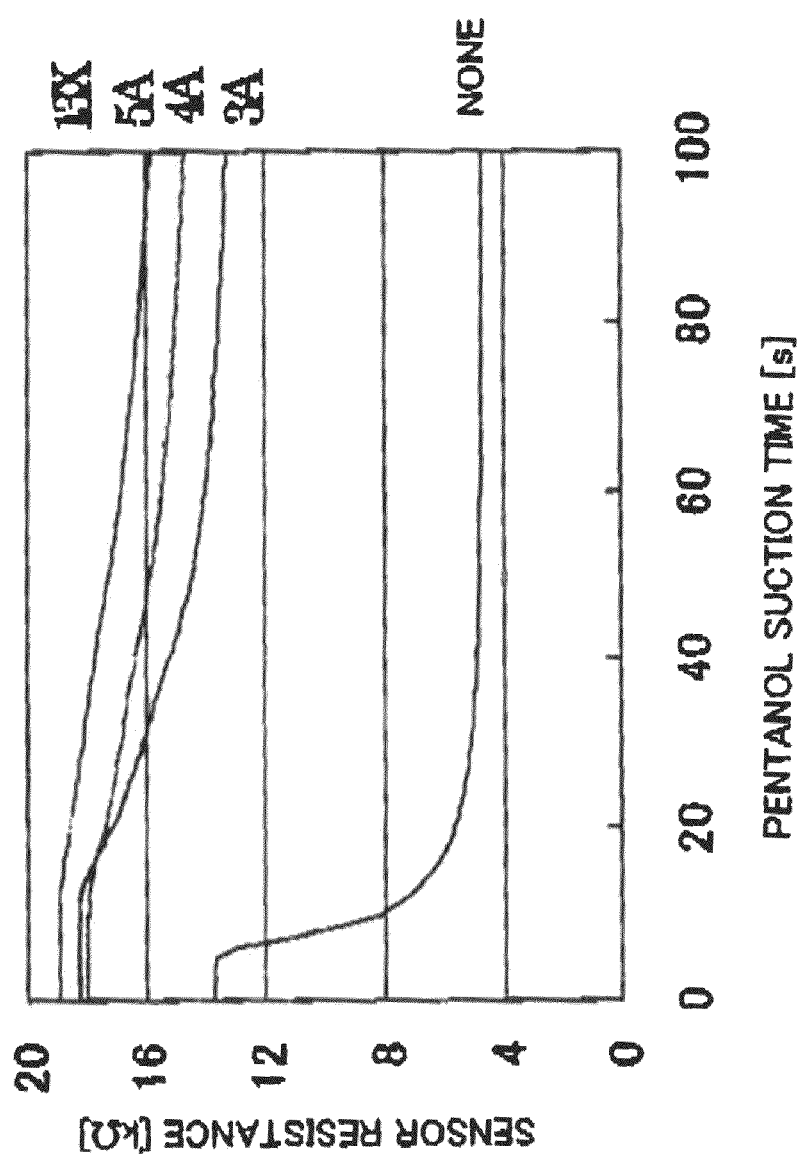
FIG. 5 is a graph illustrating data of an absorption time/sensor resistance of pentanol of 100 ppm that is obtained by actually using a smell separating/detecting apparatus shown in FIG. 3.

FIG. 5 shows data of an absorption time of pentanol of 100 ppm/sensor resistance that is actually obtained. The used oxide semiconductor gas sensor shows a resistance value of about 20 k( in clean air. In FIG. 5, a response curve that is obtained by a passage system where sample gas reaches the sensor without passing through the column is indicated as "none", and response curves in passage systems that pass through the columns where the molecular sieves of 3A, 4A, 5A, and 13X are filled are represented as "3A", "4A", "5A", and "13X", respectively. In the case of the response curve of "none" that does not pass through the column, since the sample gas reaches the surface of the gas sensor without being hindered, it is observed that the change in the sensor resistance value starts immediately after sample absorption starts and decreases rapidly.

In contrast, in the passage systems that pass through the columns, the smell materials pass through the columns and reach the gas sensor when the smell materials are not absorbed into the molecular sieves, and thus the resistance value decreases. However, in the response curves in the passage systems that pass through the columns, the responses are later and attenuations are more moderate as compared with the case of the passage system of "none". This is considered to be because the sample gas passes through the clogged column and the path of the sample gas is physically hindered. When the smell material is absorbed into the molecular sieve, since the smell material is trapped in the pore of the molecular sieve, the smell material does not reach the gas sensor and the change in the resistance value does not appear.

In the characteristic evaluations of (1) to (4), a smell material was measured by reading an initial value (t=0 s) of gas sensor resistance and a value (t=100 s) after a smell material response, and calculating the ethanol equivalent concentration of the smell material using the ethanol response characteristic of FIG. 3.

[Result of a Characteristic Evaluation Test]

(1) Evaluation Result of Separation Performance Based on Molecule Sizes (Single Sample)

Figure 8A:
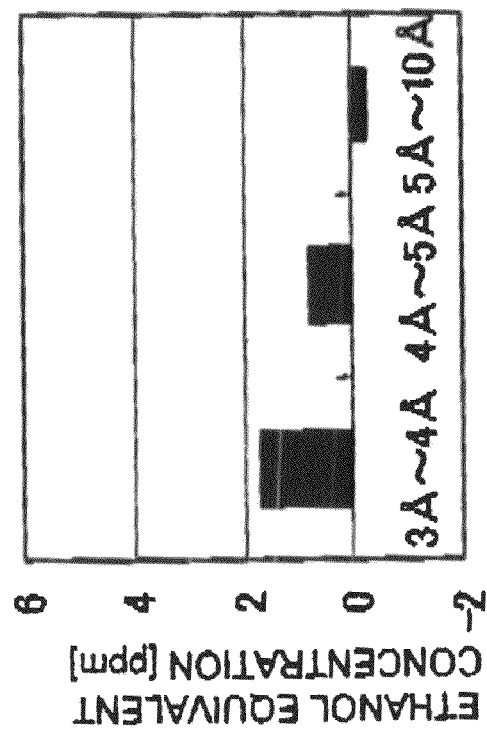
FIG. 8 is a graph illustrating a result that is obtained when a single component of acetic acid of 100 ppm is measured as a sample, using a smell separating/detecting apparatus shown in FIG. 3.
Figure 8B:
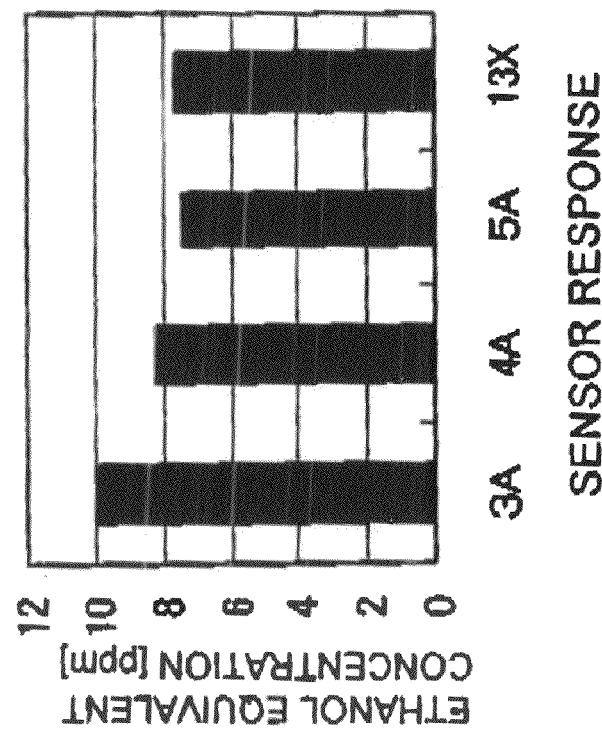

Results of measuring a single component of each of ethanol, pentanol, acetic acid of 100 ppm as a sample are shown in FIGS. 6 to 8, respectively. FIGS. 6 to 8(a) show ethanol equivalent concentrations, which are calculated from sensor responses when passing columns in which the molecular sieves of 3A, 4A, 5A, and 13X are filled, as "3A", "4A", "5A", and "13X", respectively. FIGS. 6 to 8(b) show concentrations of smell materials contained in molecules of the respective molecule size ranges, which are calculated based on data of FIGS. 6 to 8(a).

As described above, the molecular sieve "4 A" traps a chemical material that has a molecule size of 3 to 4 Å, but the molecular sieve "3A" cannot trap a chemical material having a molecule size of 3 Å or more. Accordingly, the content of the chemical material having a molecule size of 3 to 4 Å in the sample can be calculated by subtracting a value of "4A" from a value of "3A" in FIGS. 6 to 8(a). In the same way, the concentrations of the chemical materials that have the molecule sizes of 4 to 5 Å and 5 to 10 Å in FIGS. 6 to 8(b) are calculated.

Referring to the result of the ethanol equivalent concentration that is shown in FIG. 6(b), it can be seen that the concentration of the chemical material having the molecule size in the range of 4 to 5 Å is high. Actually, the molecule size of ethanol is 4.08 Å as shown in Table 1, and thus it can be seen that separation according to the molecule sizes can be achieved by the smell separating/detecting apparatus of the present invention. In this case, it should be noted that, if it is considered that ethanol is not trapped in 3A since ethanol has a molecule size larger than the pore of 3A, the gas concentration of the sample gas will not be changed even when the sample gas passes through the column where the molecular sieve of 3A is filled and the gas sensor response will show 100 ppm. However, in 3A of FIG. 6(a), the gas sensor response does not show 100 ppm because some ethanol is absorbed into the surface of the molecular sieve instead of the pore thereof. Surface absorption of a gas component is deemed to be non-specifically generated in any molecular sieve, and is offset when a difference is calculated. For this reason, the result of FIG. 6(b) is not affected by the surface absorption of the gas component.

In the same way, in the case of pentanol (molecule size of 6.34 Å) in FIG. 7(b), the concentration of the chemical material having the molecule size in a range of 5 to 10 Å is high, and in the case of acetic acid in FIG. 8(b) (molecule size of 3.16 Å), the concentration of the chemical material having the molecule size in a range of 3 to 4 Å is high. Accordingly, the smell separating/detecting apparatus shown in FIG. 3 can separate and detect the smell materials based on the molecule sizes in a sample of a single component.

(2) Evaluation Result of Separation Performance Based on Molecule Sizes (Mixed Sample)

Figure 9A:
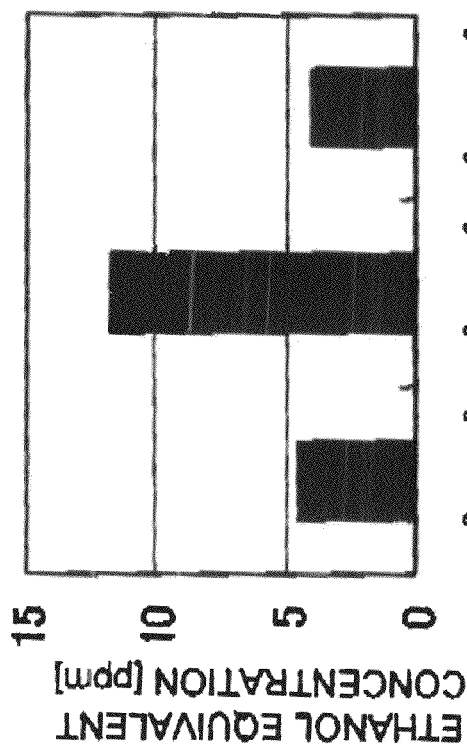
FIG. 9 is a graph illustrating a detection example with respect to a sample where two components including ethanol and pentanol are mixed, using a smell separating/detecting apparatus shown in FIG. 3.
Figure 9B:
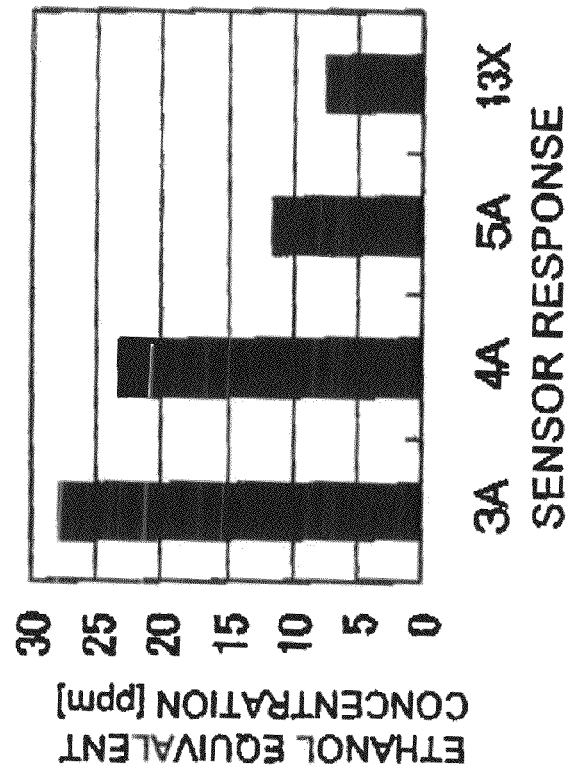
Figure 10A:
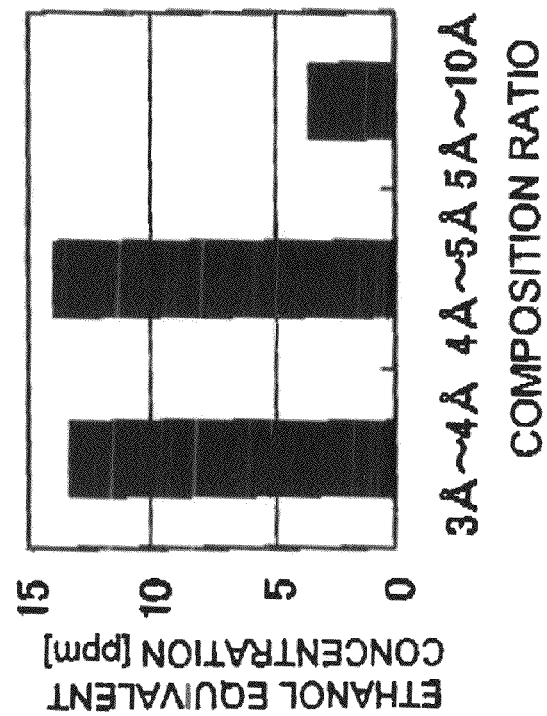
FIG. 10 is a graph illustrating a detection example with respect to a sample where three components including ethanol, pentanol, and acetic acid are mixed, using a smell separating/detecting apparatus shown in FIG. 3.
Figure 10B:
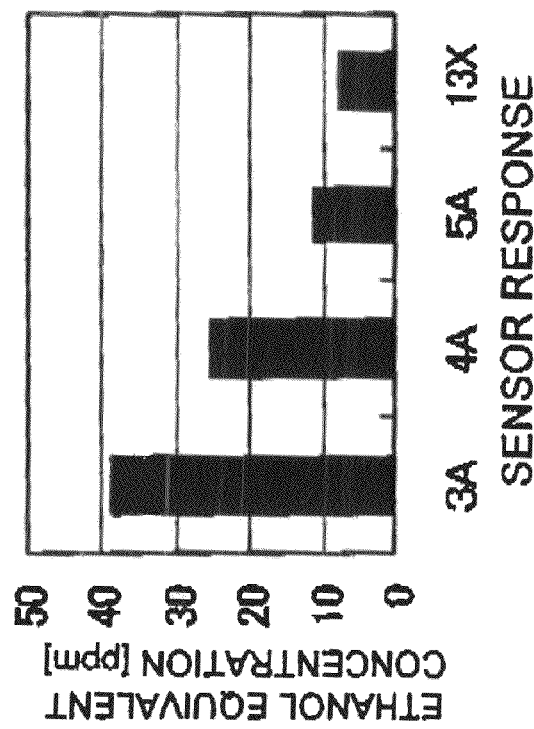

FIGS. 9(a) and 9(b) show a result with respect to a sample where two components of ethanol and pentanol are mixed, and FIGS. 10(a) and 10(b) show a result with respect to a sample where three components of ethanol, pentanol, and acetic acid are mixed. As shown in FIG. 9(b), as compared with the measurement result of ethanol alone in FIG. 6(b), the concentration of a component having a molecule size in a range of 5 to 10 Å is high. As compared with the measurement result of pentanol alone in FIG. 7(b), the concentration of a component having a molecule size in a range of 4 to 5 Å is high. That is, it can be seen that in the portion of the molecule size in a range of 5 to 10 Å, pentanol can be independently detected, and in the portion of the molecule size in a range of 4 to 5 Å, ethanol can be independently detected. Referring to FIG. 10(b), as compared with the case of the sample where ethanol and pentanol are mixed in FIG. 9(b), the concentration of a component having a molecule size in a range of 3 to 4 Å is high, and it can be said that acetic acid is detected. As a result, it is verified that the smell separating/detecting apparatus shown in FIG. 3 sufficiently has a function of performing separation and detection based on molecule sizes even in a mixed sample.

Figure 11:
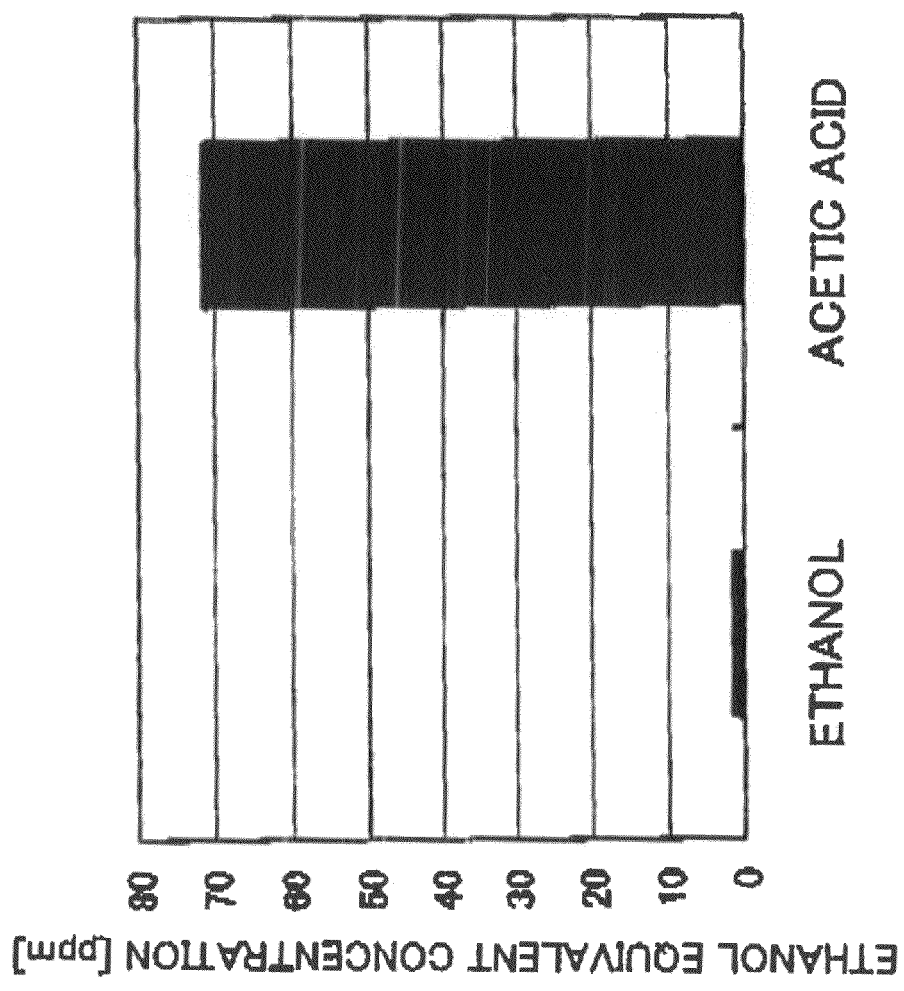
FIG. 11 is a graph showing that acid materials can be separated by using a passage of an alkali bead of a smell separating/detecting apparatus shown in FIG. 3, based on the presence or absence of an acid functionality in sample molecules, and shows a result that is obtained by calculating a concentration of acid materials in a sample indicated by a smell sensor 12, when the sample is ethanol of 100 ppm and when the sample is acetic acid of 100 ppm.

(3) Evaluation Result of Separation Performance Based on the Presence or Absence of an Acid Functionality A result that is obtained by verifying a function of separating an acid material that the smell separating/detecting apparatus shown in FIG. 3 has, using a passage of an alkali bead and based on the presence or absence of an acid functionality in a sample molecule, is shown in FIG. 11. FIG. 11 shows a calculation result of an acid material concentration in each sample that the smell sensor 12 shows with respect to a single sample of each of ethanol and acetic acid that are prepared to have the amount of 100 ppm. The smell sensor 12 has an excellent response with respect to acetic acid that is an organic acid and a high acid material concentration is shown.

However, because ethanol is not an acid material, little response as an acid material is shown with respect to ethanol by using the smell sensor 12. Accordingly, it is verified that the smell separating/detecting apparatus shown in FIG. 3 sufficiently has a function of separating and detecting an acid material.

(4) Evaluation Result of Body Smell Measurement Performance

Figure 12:
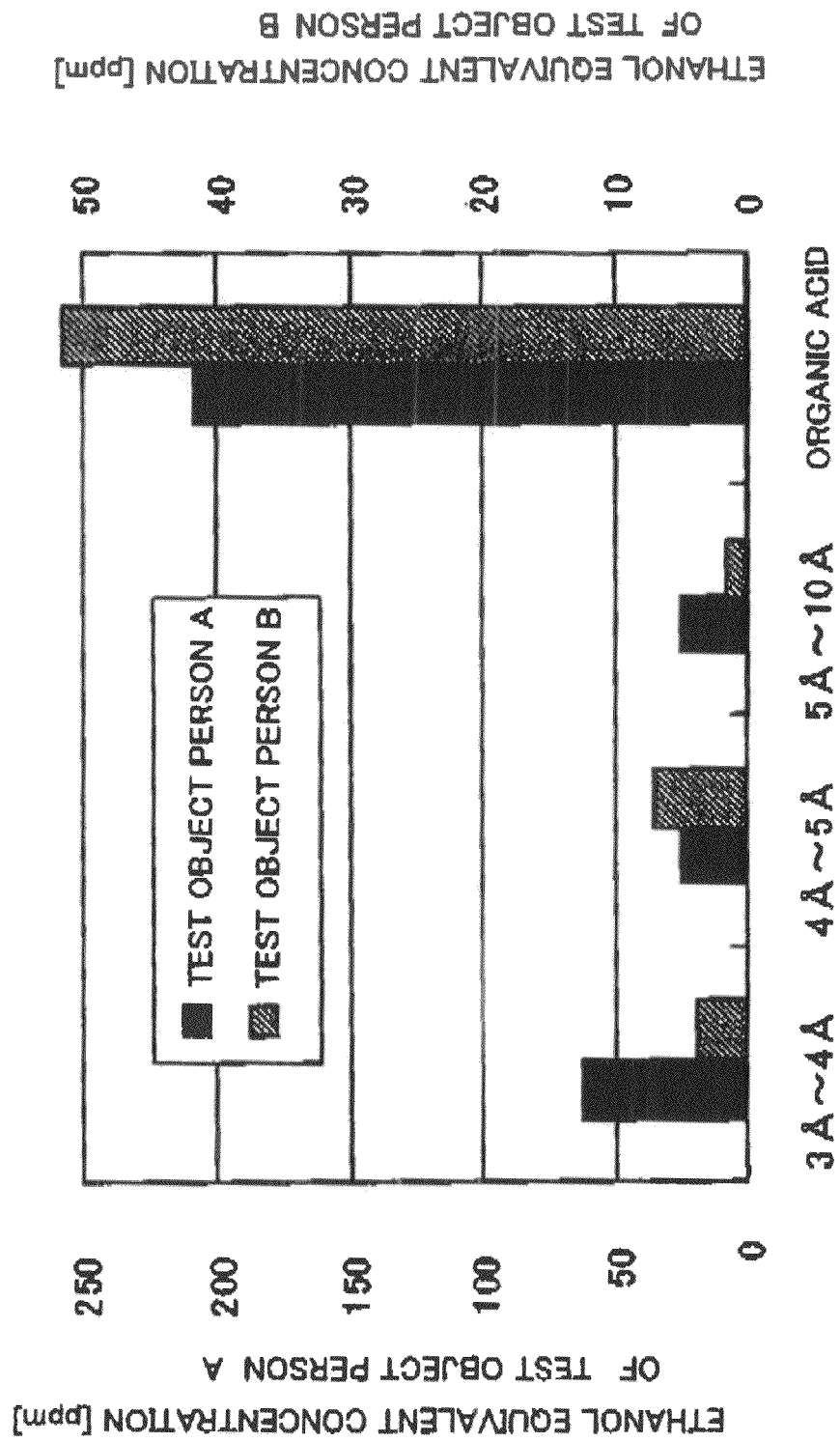
FIG. 12 is a graph illustrating a result that is obtained by measuring body smells of test object persons A and B.
Figure 15E:
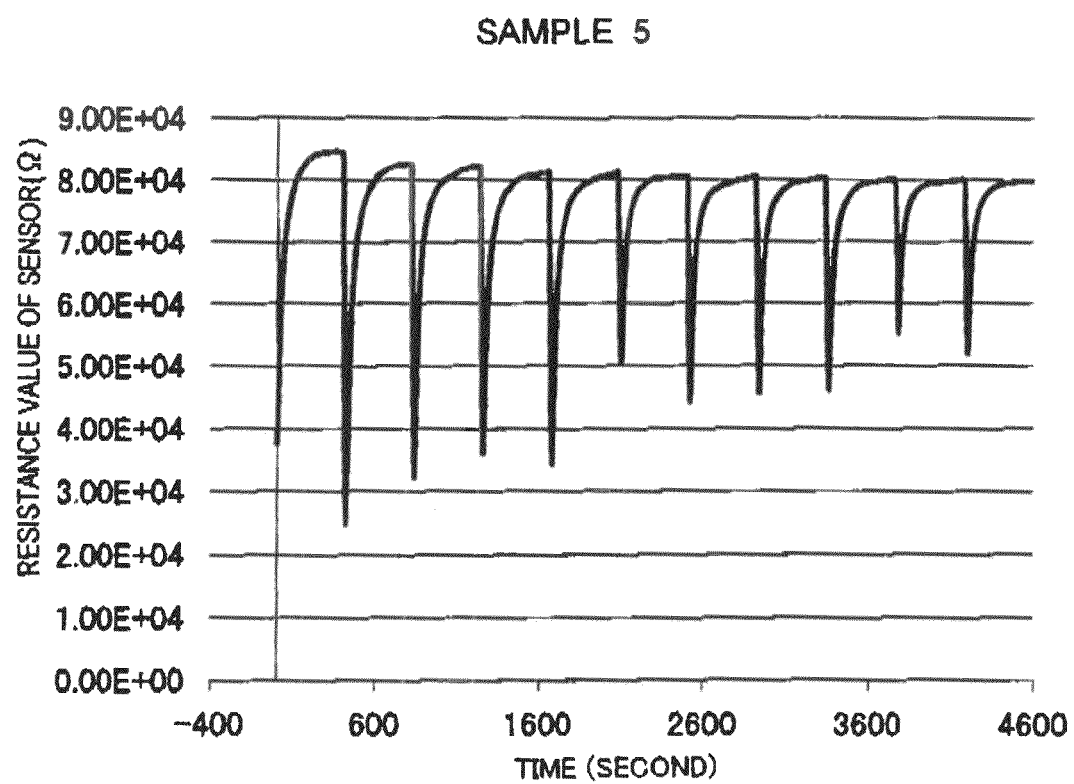
FIG. 15(e) is a graph of a resistance value that a smell sensor 12 indicates with respect to sample gas 5 of a body smell.
Figure 15F:
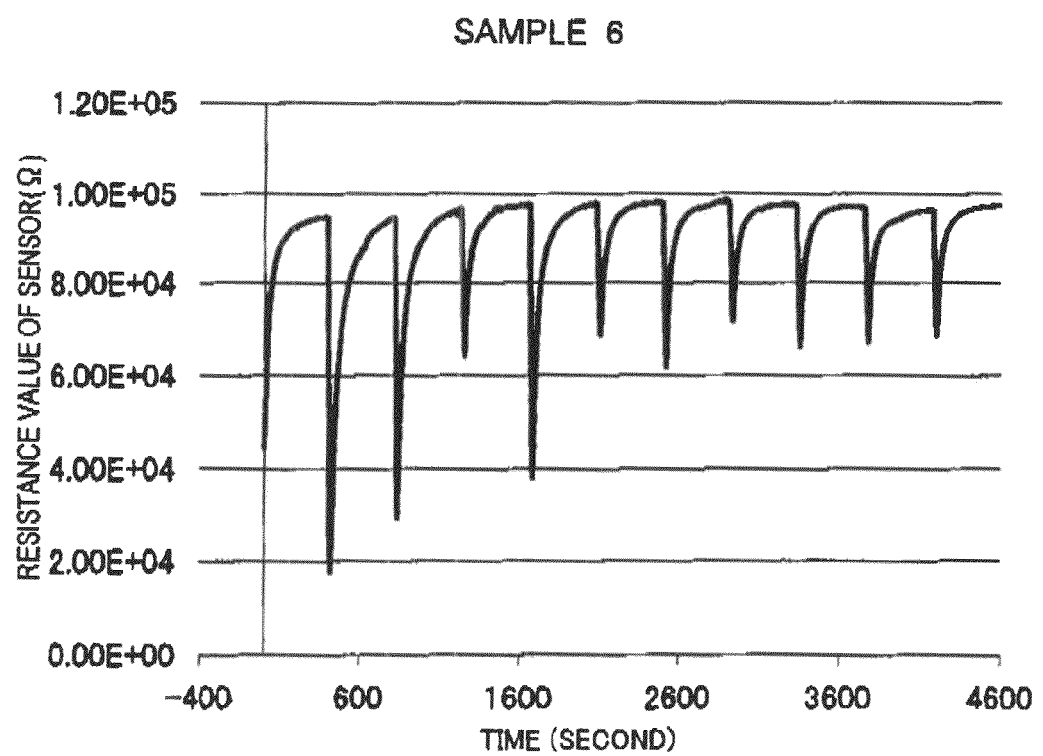
FIG. 15(f) is a graph of a resistance value that a smell sensor 12 indicates with respect to sample gas 6 of a body smell.
Figure 15G:
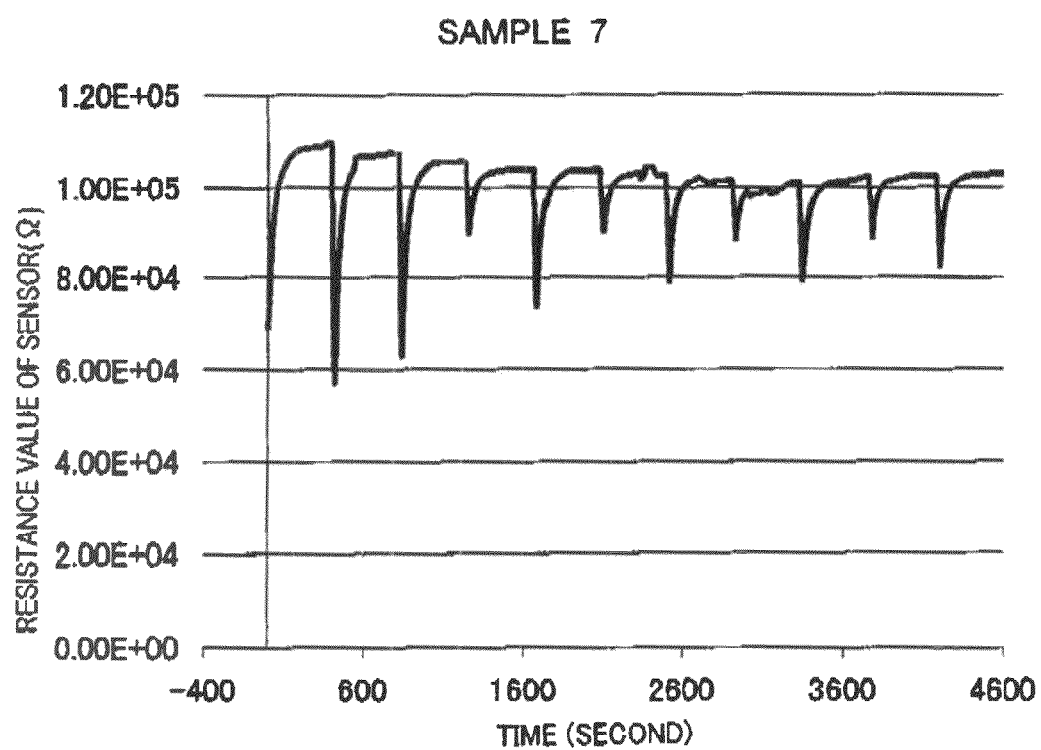
FIG. 15(g) is a graph of a resistance value that a smell sensor 12 indicates with respect to sample gas 7 of a body smell.
Figure 15H:
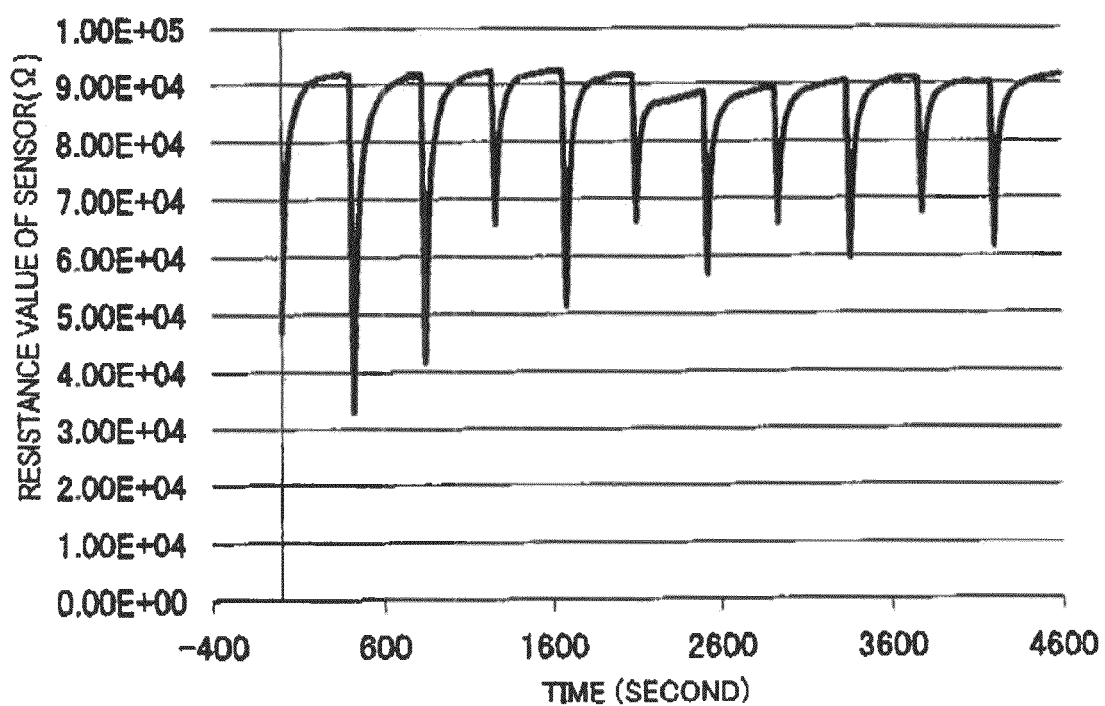
FIG. 15(a) is a graph of a resistance value that a smell sensor 12 indicates with respect to sample gas 1 of a body smell.
FIG. 15(b) is a graph of a resistance value that a smell sensor 12 indicates with respect to sample gas 2 of a body smell.
FIG. 15(c) is a graph of a resistance value that a smell sensor 12 indicates with respect to sample gas 3 of a body smell.
FIG. 15(d) is a graph of a resistance value that a smell sensor 12 indicates with respect to sample gas 4 of a body smell.
FIG. 15(*h*) is a graph of a resistance value that a smell sensor 12 indicates with respect to sample gas 8 of a body smell.

FIG. 12 shows body smell measurement results of test object persons A and B. With respect to the test object person A, the concentration of the smell materials having the molecule size of 4 to 5 Å is lower than the concentration of the materials having other molecule sizes. In contrast, with respect to the test object person B, the result to the contrary is obtained. This can be regarded that an individual person has a unique smell pattern and it can be expected that the "odor type" is reflected. According to the above result, since it is verified that the smell separating/detecting apparatus shown in FIG. 3 has a function of analyzing that a composition ratio of smell materials constituting a body smell is different for each person, it is possible to configure the biometrics sensor of the present invention using this apparatus.

As described above, the smell separating/detecting apparatus is manufactured using the molecular sieve and the alkali bead. The function of sieving molecules is effectively achieved in any of a single component sample and a mixed component sample of organic acids and alcohols that are considered to be largely associated with the "odor type" of the body smell of the living body, and molecules of individual sizes and acids are successfully detected. Further, the smell of an individual person is actually measured using the smell separating/detecting apparatus shown in FIG. 3 and it is verified that a different smell pattern exists for each person.

In the above configuration example, the molecular sieve portion is composed of channels of a total of five kinds of filters for gas that include an alkali bead and four kinds of molecular sieves. Since various gas components need to be detected when the smell is actually measured, various kinds of filters for gas can be combined and the number of channels of filters for gas can be increased in accordance with gas components of the detection object. Further, since the alkali bead has weak acid absorption ability, it is possible to improve separation performance with respect to organic acids of the molecular sieve portion by increasing the filling amount of the alkali bead.

Further, in recent years, it is reported that a second olfactory receptor as a receptor of an amine system is discovered, and the amines may be used as an important element in identifying individuals. However, also in the case of the amines, the smell separating/detecting apparatus shown in FIG. 3 may be configured using the thiol film (FIG. 14(c)) formed as a monomolecular film on a surface of a metal such as gold, instead of the molecular sieve 6 or the alkali bead 7 shown in FIG. 3, to constitute the molecular sieve portion of the biometrics sensor of the present invention.

As such, in order to selectively pass through or absorb a specific gas component contained in air being an analysis subject, the molecular sieve portion that constitutes the biometrics sensor of the present invention can be configured by combining filters for gas of a plurality of kinds according to the air being an analysis subject.

[Personal Authentication Test Based on Smells]

The present invention has a function of extracting a characteristic of a smell such as a body smell of an authentication object person, and using the smell characteristic for authentication. Accordingly, the personal authentication test is performed using the smell separating/detecting apparatus shown in FIG. 3, as described below.

(1) Trapping of Sample Gas

First, smell-free T-shirts are prepared. Then, the T-shirts are worn by test object persons A to E for one night. As a result, the T-shirts are impregnated with body smells of the test object persons A to E, respectively. Then, the worn T-shirts are sealed in individual sample bags to be then heated for two hours at a temperature of about 60° C. using an oven such that the smell materials of the test object persons impregnated in the T-shirts are volatilized and filled into the sample bags as gas. In this way, sample gases of eight kinds are trapped.

In order to examine reproducibility of a personal authentication test, among the sample gases of the eight kinds, the samples 1 to 3 are prepared for the body smell of the test object person A, and the samples 4 and 5 are prepared for the body smell of the test object person B. The relation between the test object persons and the trapped sample gases is shown as follows.

TABLE 2

| Test object person | Trapped body smell sample |
|---|---|
| A | 1, 2, 3 |
| B | 4, 5 |
| C | 6 |
| D | 7 |
| E | 8 |

(2) Test Method

The time during which each sample gas is absorbed into a filter for gas is set as 20 seconds. For 400 seconds before and after this period, smell-free air is circulated through the passage 8 to clean the material absorbed into the smell sensor 12. After restoring the smell sensor 12 to a reference state, sample gas is absorbed into another filter for gas by switching the passage. The passage is switched in the following order, and a resistance value of the smell sensor 12 is measured by using the sample gases 1 to 8.

Clean smell sensor 12→Circulate sample gas without passing through filter for gas→Clean smell sensor 12→Absorb in only alkali bead 7→Clean smell sensor 12→Absorb in only molecular sieve 3A→Clean smell sensor 12→Absorb in molecular sieve 3A and alkali bead 7→Clean smell sensor 12→Absorb in only molecular sieve 4A→Clean smell sensor 12→Absorb in molecular sieve 4A and alkali bead 7→Clean smell sensor 12→Absorb in only molecular sieve 5A→Clean smell sensor 12→Absorb in molecular sieve 5A and alkali bead 7→Clean smell sensor 12→Absorb in only molecular sieve 13X→Clean smell sensor 12→Absorb in molecular sieve 13X and alkali bead 7→Clean smell sensor 12

The changes in the resistance values of the sensor 12 in regards to the sample gases 1 to 8 are shown in FIGS. 15(a) to 15(h).

(3) Analysis of Test Result

Figure 16A:
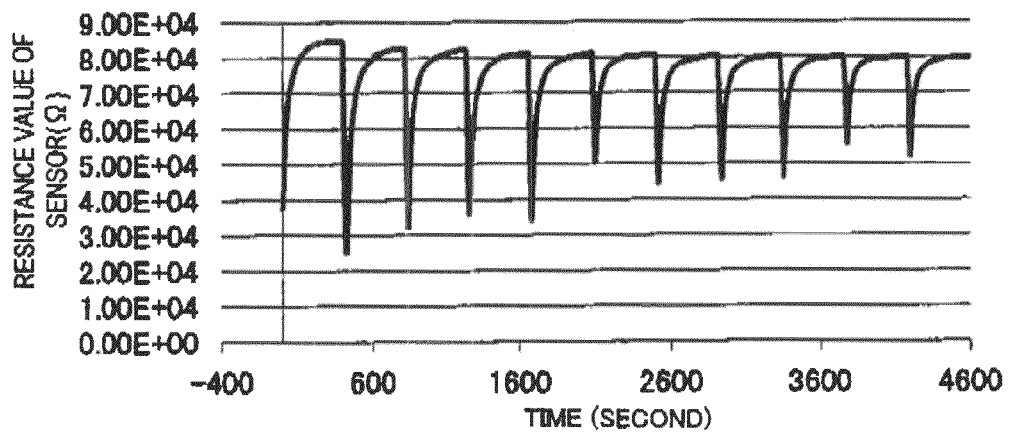
FIG. 16(*a*) is a graph illustrating a correspondence relation between minimum values of resistance values and filters for gas.

The resistance value of the smell sensor 12 is decreased by the smell material contacting with the smell sensor 12, and the resistance value is increased by cleaning the smell sensor 12 with smell-free air. For this reason, as shown in FIGS. 15(a) to 15(h), a number of minimum values are observed in a temporal change of the resistance value. The minimum values of the resistance value correspond to the passage to the filters for gas that absorb the sample gas. The relation between the minimum values of the resistance value and the filters for gas is shown in FIG. 16(a). In FIG. 16(a) and subsequent figures, the alkali bead 7 and the molecular sieves 3A, 4A, 5A, and 13X are represented by "AB", "3 Å", "4 Å", "5 Å", and "10 Å". Further, when the filter for absorbed gas is composed of the molecular sieve and the alkali bead, it is represented by, for example, "3 Å+AB".

Based on the minimum values that are shown in FIGS. 15(a) to 15(h), the relative concentration of the smell materials can be calculated using the following calculation method.

Figure 16B:
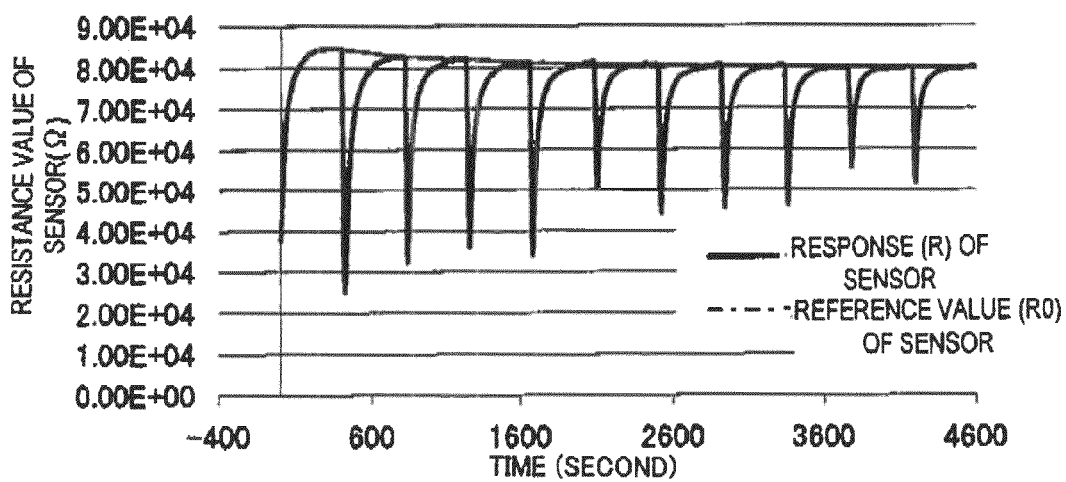

First, in each of FIGS. 15(a) to 15(h), resistance values immediately before switching from introduction of smell-free air into introduction of sample gas are determined. Next, in each of FIGS. 15(a) to 15(h), the determined resistance value points are connected with a smooth continuous curve, and the curve is used as a reference value curve R0 of the sensor. The relation between the response curve (R) indicating the temporal change in the resistance value of the sensor and the reference value curve (R0) of the sensor is shown in FIG. 16(b).

Where the resistance value of the smell sensor is r and the reference value on the reference value curve (R0) corresponding to the resistance value r is $r_0$, log (c) of the concentration c of gas is proportional to an absolute value of log ($r_0/r$). In this case, a method for determining r and $r_0$ have to be decided, and the concentration of gas that is derived from only one point in the graph is vulnerable to a noise. Accordingly, an average of ($r_0/r$) is calculated for the resistance values r before and after each minimum value of the resistance values of the sensor. In addition, a logarithmic value is calculated for the average by using the following equation.

$$z = \log\{1/(t_2-t_1) \times \Sigma(r/r_0)\} \qquad \text{Equation (1)}$$

Herein, $t_1$ represents the time when introduction of sample gas where a minimum value of a considered resistance value were shown started, and $t_2$ represents the time when circulation of smell-free air, which was performed immediately after the introduction of the sample gas was completed, started.

Figure 16C:
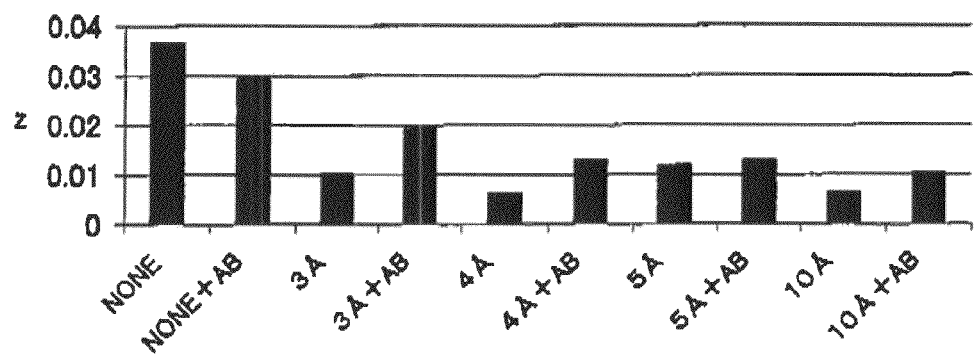
Figure 17D:
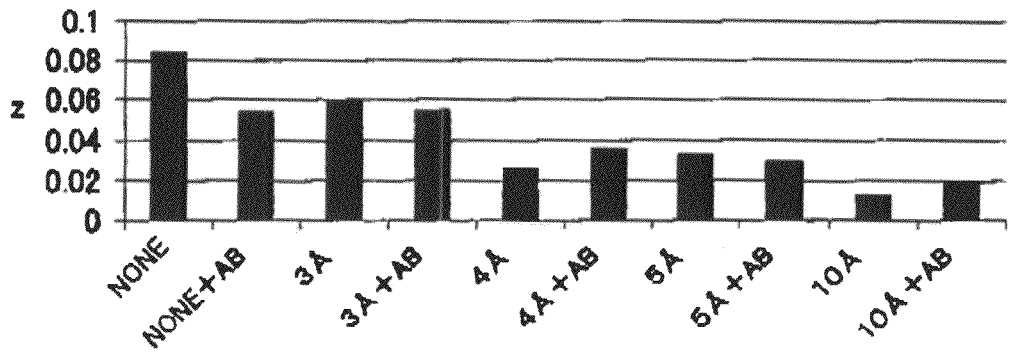
FIG. 17(*a*) is a graph illustrating a relative concentration of a smell material contained in sample gas 1 of a body smell, which is calculated based on FIG. 15(*a*).
Figure 17E:
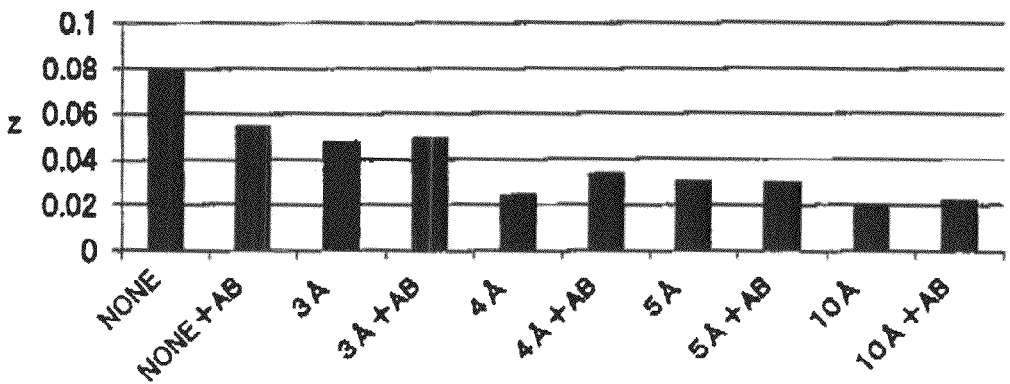
Figure 17F:
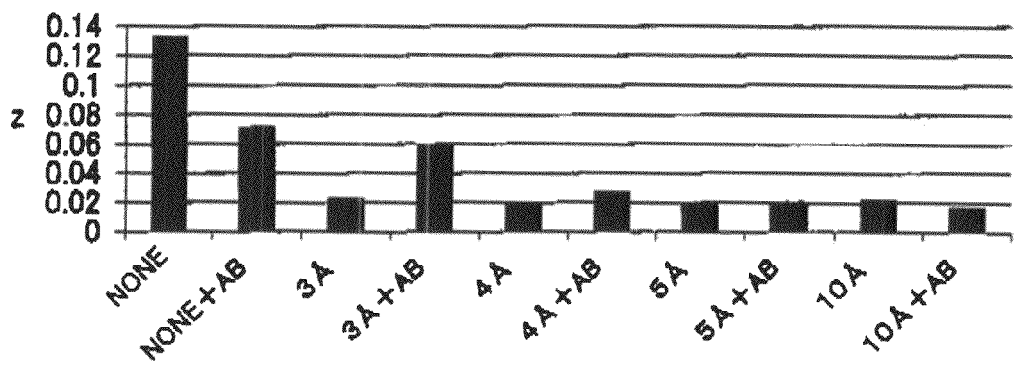
Figure 17G:
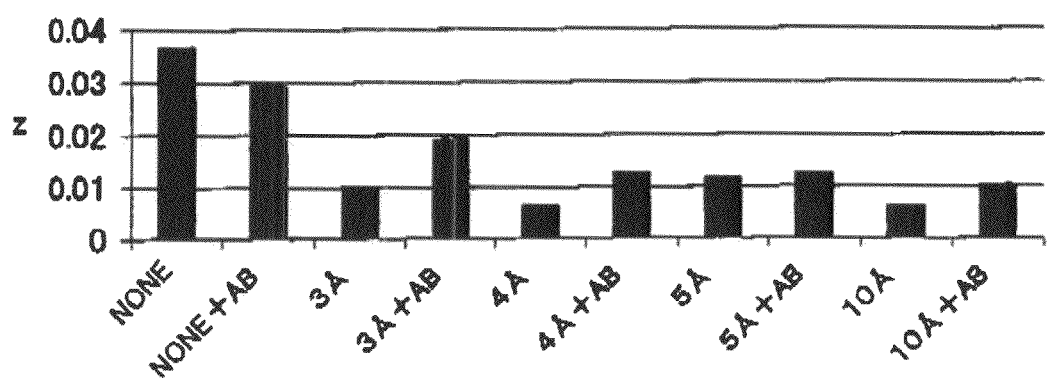
Figure 17H:
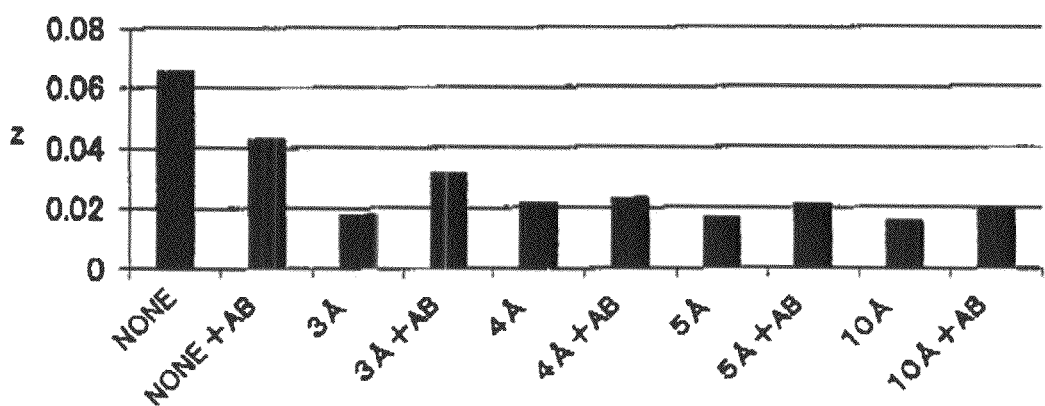

Each minimum value in the resistance values of the smell sensor corresponds to a resistance value that is related to a passage where sample gas is introduced, that is, a filter for gas where sample gas is introduced. FIG. 16(c) is a graph illustrating a relative concentration z of a smell material contained in sample gas, which is calculated from Equation (1) based on FIG. 16(b). In FIG. 16(c), if a value of z is high, the smell material of the molecule size corresponding to the filter for gas is detected and the concentration thereof is high. FIGS. 17(a) to 17(h) are graphs illustrating a relative concentration z of a smell material that is contained in each of sample gases 1 to 8 of a body smell, which is calculated based on each of FIGS. 15(a) to 15(h).

Since gas components are different for each sample, z of respective samples have different distributions, as shown in FIGS. 17(a) to 17(h). In addition, since a body smell of the same person has a specific gas distribution, the individual persons can be distinguished by comparing the distributions of the relative concentrations z of the smell materials.

Figure 18:
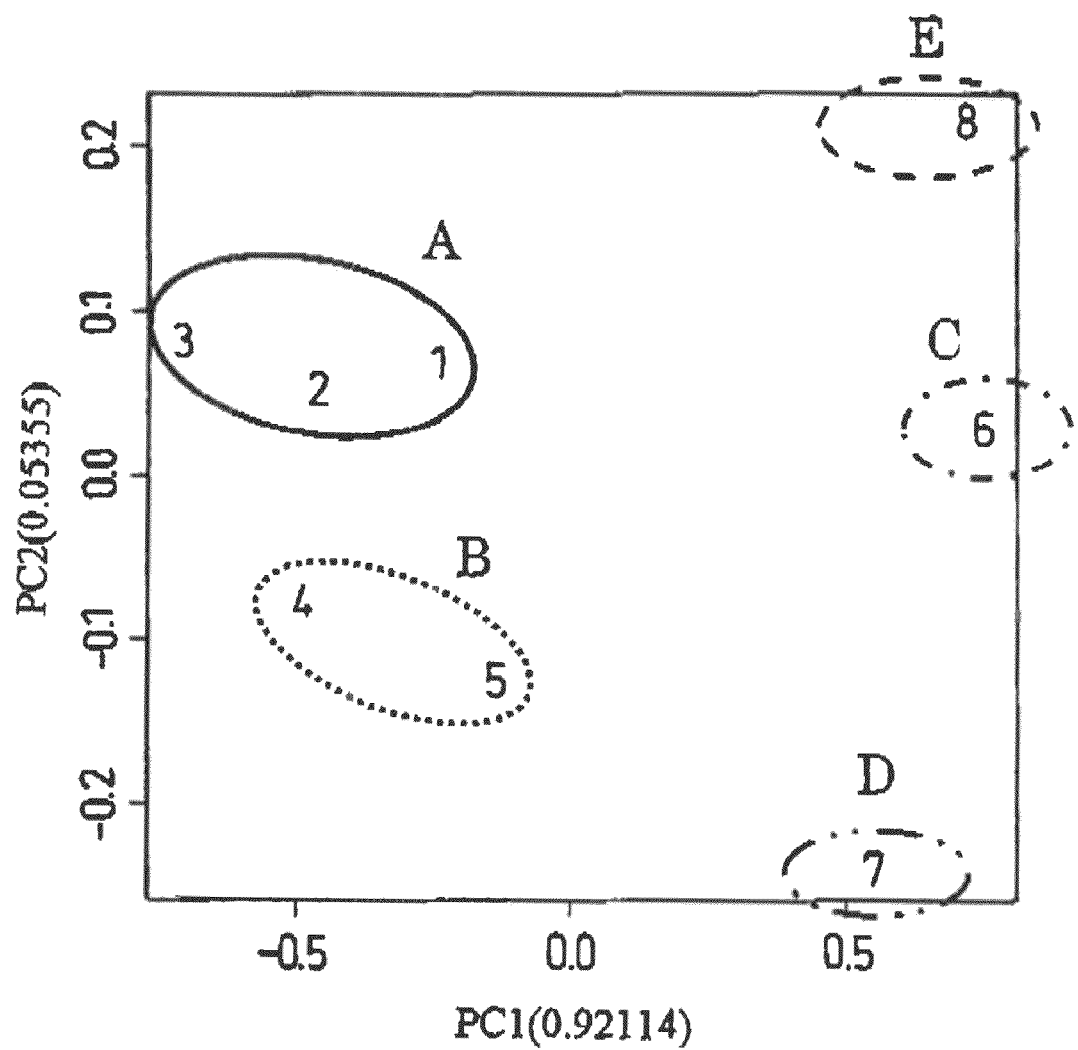
FIG. 18 is a graph illustrating a result that is obtained by analyzing data of sample gas of a body smell as a main component, except for data of a resistance value of a smell sensor in the case of using a passage through an alkali bead, in regards to sample gases 1 to 8 of body smell.

With respect to the eight samples, except for data of a resistance value of the smell sensor in the case where the passage passing through the alkali bead is used, the result of FIG. 18 is obtained by analyzing data of the relative concentration z of the smell material as a main component. The horizontal axis and the vertical axis of FIG. 18 represent magnitudes of the first main component (PC1) and the second main component (PC2) of the sample gas, respectively. The contribution ratios of PC1 and PC2 are 0.92114 and 0.05355, respectively.

In PC1 and PC2, a variable that maximizes a dispersion of a variation of data is determined by a main component analysis, and obtained by the following linear conversion, $$PC1 = a11 \times (\text{smell data 1}) + \ldots + a15 \times (\text{smell data 5})$$

$$PC2 = a21 \times (\text{smell data 1}) + \ldots + a25 \times (\text{smell data 5})$$

In the case of this test, the smell data 1 is data from a passage where a molecular sieve does not exist, the smell data 2 is data of the molecular sieve 3 Å, the smell data 3 is data of the molecular sieve 4 Å, the smell data 4 is data of the molecular sieve 5 Å, and the smell data 5 is data of the molecular sieve 10 Å.

In the above equations, a11, a12, a13, a14, and a15 are determined as 0.30254463, −0.81764344, 0.05372084, −0.02485475, and 0.48623272, respectively. Further, a21, a22, a23, a24, and a25 are determined as −0.11814801, −0.03334846, 0.81285744, −0.56034606, and −0.10101491, respectively. The values that are obtained in the above way are shown in FIG. 18.

In FIG. 18, reference numerals 1 to 8 denote the sample gases 1 to 8. In this case, if the samples have a short distance therebetween, the distributions of z in the samples are close to each other. It can be seen from FIG. 18 that samples extracted from the same test object person exist at the close locations. In addition, it can be seen that the z distributions of the individual test object persons are different from each other. The result indicates that the present invention has a function of extracting a characteristic of a smell such as a body smell of the authentication object person and using the smell characteristic for authentication.

In the above description, the case where the present invention is applied to the authentication system has been described. However, when survivors are searched for at the time of a disaster, data at the time of the disaster is used as database prestored in the data processing section. The data at the time of the disaster is not data of the individual person, but is data that can easily discriminate people and animals from each other, such as the data on the smell of the blood. Further, when the present invention is used in medical diagnosis, oral smell data or body smell data for each disease is prestored in the data processing section. Further, oral smell data or body smell data when a measurement object person is in health is stored, and the smell data is compared with oral smell data or body smell data that is actually measured at the time of diagnosis, thereby determining a health state of the measurement object person.

INDUSTRIAL APPLICABILITY

As described above, the biometrics sensor of the present invention selectively extracts a specific gas component contained in air in the vicinity of the measurement object person and compares the detection result and the prestored detection result. For this reason, since the biometrics sensor of the present invention can remotely measure biological information, the biometrics sensor can be easily used in searching for survivors or medical diagnosis. Further, the biometrics sensor of the present invention can be used in a personal authentication system of an electronic hardware together with another authentication method, which results in improving security in managing information.

The invention claimed is:
1. A biometrics sensor comprising:
a sucking section that sucks air in the vicinity of a measurement object person;

a molecular sieve portion that comprises a molecular sieve that selectively passes or absorbs a specific gas component contained in the sucked air on the basis of molecule sizes and an alkali bead that selectively passes or absorbs a specific gas component contained in the sucked air on the basis of a difference in the presence or absence of an acid functionality;

a gas detecting section that detects a concentration of a constituent component of gas passed through the molecular sieve portion or the specific gas component selectively passed through the molecular sieve portion or the specific gas component selectively absorbed into the molecular sieve portion and remaining in the gas passed through the molecular sieve portion; and a data processing section that compares the detection result of the gas detecting section and a prestored detection result.

2. The biometrics sensor according to claim 1,
wherein the biometrics sensor is used in a personal authentication system used in an electronic hardware,
the measurement object person is an authentication object person,
the molecular sieve portion absorbs organic acids, alcohols or amines and discharges other gas components,
the gas detecting section selectively detects a predetermined gas component from the discharged gas components, and
the data processing section includes an operation section and a storage section, and compares a composition ratio of organic acids, alcohols or amines for each authentication object person with a composition ratio obtained from the prestored detection result to perform determination or probabilistic determination on the authentication object person.

3. The biometrics sensor according to claim 2,
wherein the molecular sieve portion comprises a filter for gas that separates the organic acids, the alcohols or the amines based on a difference in molecule sizes, and a filter for gas that separates the organic acids, the alcohols or the amines based on the presence or absence of an acid functionality or an amine group, and
a smell detector is used as the gas detecting section.

4. The biometrics sensor according to claim 3,
wherein (i) the filter for gas that separates the organic acids, the alcohols or the amines based on the difference in the molecule sizes includes multiple filters, wherein each of the multiple filters comprises at least one absorptive material having an absorption amount depending on the molecule sizes and is arranged in parallel according to said molecule sizes,
wherein (ii) the filter for gas that separates the organic acids, the alcohols or the amines based on the presence or absence of the acid functionality or the amine group absorbs the organic acids, the alcohols or the amines to a material having a strongly basic material film formed on a surface thereof or a material having a strongly acidic material film formed on a surface thereof to filtrate the gas, and
wherein the biometrics sensor further comprises a switching section that individually connects the gas detecting section to each of the multiple filters of the filter (i) and to the filter (ii).

5. A biometrics sensor comprising:
a sucking section that sucks air in the vicinity of a measurement object person;
a molecular sieve portion that selectively passes or absorbs a specific gas component contained in the sucked air;
a gas detecting section that detects a concentration of a constituent component of gas passed through the molecular sieve portion or the specific gas component selectively passed through the molecular sieve portion or the specific gas component selectively absorbed into the molecular sieve portion and remaining in the gas passed through the molecular sieve portion; and
a data processing section that compares the detection result of the gas detecting section and a prestored detection result,
wherein the biometrics sensor is used in a personal authentication system used in an electronic hardware,
the measurement object person is an authentication object person,
the molecular sieve portion absorbs organic acids, alcohols or amines and discharges other gas components,
the gas detecting section selectively detects a predetermined gas component from the discharged gas components, and
the data processing section includes an operation section and a storage section, and compares a composition ratio of organic acids, alcohols or amines for each authentication object person with a composition ratio obtained from the prestored detection result to perform determination or probabilistic determination on the authentication object person,
wherein the molecular sieve portion comprises a filter for gas that separates the organic acids, the alcohols or the amines based on a difference in molecule sizes, and a filter for gas that separates the organic acids, the alcohols or the amines based on the presence or absence of an acid functionality or an amine group, and
a smell detector is used as the gas detecting section,
wherein (i) the filter for gas that separates the organic acids, the alcohols or the amines based on the difference in the molecule sizes includes multiple filters, wherein each of the multiple filters comprises at least one absorptive material having an absorption amount depending on the molecule sizes and is arranged in parallel according to said molecule sizes,
wherein (ii) the filter for gas that separates the organic acids, the alcohols or the amines based on the presence or absence of the acid functionality or the amine group absorbs the organic acids, the alcohols or the amines to a material having a strongly basic material film formed on a surface thereof or a material having a strongly acidic material film formed on a surface thereof to filtrate the gas, and
wherein the biometrics sensor further comprises a switching section that individually connects the gas detecting section to each of the multiple filters of the filter (i) and to the filter (ii).

* * * * *